United States Patent [19]
Sanderson et al.

[11] Patent Number: 5,744,486
[45] Date of Patent: Apr. 28, 1998

[54] PYRIDINONE THROMBIN INHIBITORS

[75] Inventors: Philip E. Sanderson, Philadelphia; Adel M. Naylor-Olsen; Dona L. Dyer, both of Lansdale; Joseph P. Vacca, Telford; Richard C. A. Isaacs, Harleysville; Bruce D. Dorsey, Maple Glen; Mark E. Fraley, North Wales, all of Pa.

[73] Assignee: Merck & Co., Inc., Rahway, N.J.

[21] Appl. No.: 829,406

[22] Filed: Mar. 31, 1997

Related U.S. Application Data

[62] Division of Ser. No. 669,189, Jun. 24, 1996, Pat. No. 5,668,289.

[51] Int. Cl.$^6$ .................... A61K 31/445; C07D 211/06
[52] U.S. Cl. .................... 514/318; 546/194; 546/208
[58] Field of Search .................... 514/318; 546/194, 546/208

[56] References Cited

U.S. PATENT DOCUMENTS 5,260,307 11/1993 Ackermann et al. .................... 514/323
5,405,854 4/1995 Ackermann et al. .................... 514/315

FOREIGN PATENT DOCUMENTS 0 509 769 A3 10/1992 European Pat. Off. .

OTHER PUBLICATIONS

Bernstein, et al., J. Med. Chem., 37, 3313–3326 "Nonpeptidic Inhibitors of Human Leukocyte Elastase . . . ", 1994.

Primary Examiner—C. Warren Ivy
Assistant Examiner—Charanjit S. Aulakh
Attorney, Agent, or Firm—Richard S. Parr; Melvin Winokur

[57] ABSTRACT

Compounds of the invention are useful in inhibiting thrombin and associated thrombotic occlusions and have the following structure:

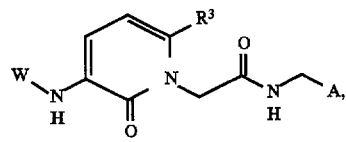

for example:

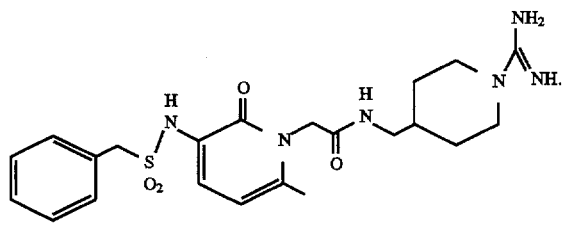

13 Claims, No Drawings

PYRIDINONE THROMBIN INHIBITORS

This is a division of application Ser. No. 08/669,189 filed Jun. 24, 1996, now U.S. Pat. No. 5,668,289.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards etal., J. Amer. Chem. Soc. (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., J. Med. Chem. Vol. 37, pages 1259–1261 (1994) describes orally active, non-peptidic inhibitors of human leukocyte elastase which contain trifluoromethylketone and pyridinone moieties.

H. Mack et al., J. Enzyme Inhibition Vol. 9, pages 73–86 (1995) describes rigid amidino-phenylalanine thrombin inhibitors which contain a pyridinone moiety as a central core structure.

SUMMARY OF THE INVETION

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Some abbreviations that may appear in this application are as follows.

| ABBREVIATIONS | |
|---|---|
| Designation | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| Activating Group | |
| HBT(HOBT or HOBt) | 1-hydroxybenzotriazole hydrate |
| Designation | Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chloride |
| EDC | 1-ethyl-3-(3-dimethylaminopropyl) carbodiimide hydrochloride |
| | Other |
| (BOC)₂O (BOC₂O) | di-t-butyl dicarbonate |
| n-Bu₄N+F– | tetrabutyl ammonium fluoride |
| nBuLi (n-Buli) | n-butyllithium |
| DMF | dimethylformamide |
| Et₃N | triethylamine |
| EtOAc | ethyl acetate |
| TFA | trifluoroacetic acid |
| DMAP | dimethylaminopyridine |
| DME | dimethoxyethane |
| LDA | lithium diisopropylamide |
| DPPA | diphenylphosphoryl azide |
| THF | tetrahydrofuran |
| DIPEA | diisopropylethylamine |
| | Amino Acid |
| Ile | Isoleucine |
| Phe | Phenylalanine |
| Pro | Proline |
| Ala | Alanine |
| Val | Valine |

DETAILED DESCRIPTION OF THE INVENTION AND PREFERRED EMBODIMENTS

Compounds of the invention are useful as thrombin inhibitors and have therapeutic value in for example, preventing coronary artery disease, and have the following structure:

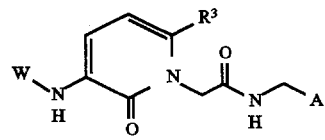

wherein W is $R^1$, $R^1OCO$, $R^1CO$, $R^1SO_2$, $(R^1)m(CH_2)_n NH_qCO$, where n is 0–4, m is 1 or 2, and q is 0 or 1, with the proviso that wherenis 1–4,qis 1 and mis 1, and wherenis 0,m is 1 or2, andqis0 or 1, and wherenis 0,m is 2andqis 0, $R^1$ can be the same or different;

$R^1$ is $R^2(CH_2)_n$, where n is 0–4, $(R^2)(OR^2)CH(CH_2)_p$, where p is 1–4, $(R^2)_2CH(CH^2)_n$, where n is 0–4 and $R^2$ can be the same or different, and wherein $(R^2)2$ can also be a ring substituent on CH represented by $C_{3-7}$ cycloalkyl, $C_{7-12}$ bicyclic alkyl, or a 5- to 7- membered mono- or bicyclic heterocyclic ring which can be saturated or unsaturated, and which contains from one to three heteroatoms selected from the group consisting of N, O and S, and $R^2O(CH_2)_p$, wherein p is 1–4;

$R^2$ is hydrogen, phenyl, unsubstituted or substituted with one or more of $C_{1-4}$ linear or branched alkyl, $C_{1-4}$ linear or branched alkoxy, halogen, trifluoromethyl, hydroxy, COOH, or $CONH_2$, naphthyl, biphenyl, a 5- to 7- membered mono- or a 9- to 10-membered bicyclic heterocyclic ring which can be saturated or unsaturated, and which contains from one to three heteroatoms selected from the group consisting of N, O and S, $COOR^6$, $C_{1-4}$ linear or branched alkyl, $C_{3-7}$ cycloalkyl, or $C_{7-12}$ bicyclic alkyl;

$R^3$ is hydrogen, $C_{1-4}$ linear or branched alkyl, $C_{3-7}$ cycloalkyl, or trifluoromethyl;

A is chosen from one of the following Radicals:

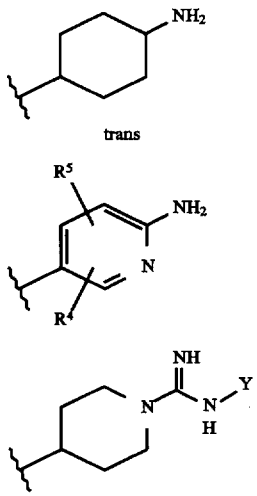

wherein $R^4$ and $R^5$ are independently H, C 1—4 linear or branched alkyl or alkoxy; $C_3$—$C_7$ cycloalkyl; halogen; or trifluoromethyl;

Y is hydrogen, hydroxy, or CN;

$R^6$ is hydrogen, or $C_{1-4}$ linear or branched alkyl, and pharmaceutically acceptable salts thereof.

A useful class of compounds is the embodiment wherein W is $R^1$ or $R^1$ $SO_2$. A further useful subclass of compounds is the embodiment wherein $R^1$ is $R^2(CH_2)_n$, $(R^2)_2CH(CH_2)_n$, phenyl, or $(phenyl)_2$—CH.

Another useful class of compounds is the embodiment wherein $R^3$ is $C_{1-4}$ linear or branched alkyl and particularly wherein $R^3$ is methyl.

Another useful class of compounds is the embodiment wherein $R^4$ is $C_{1-4}$ linear or branched alkyl and $R^5$ is methyl or hydrogen and particularly wherein $R^4$ is methyl and $R^5$ is methyl or hydrogen and most particularly when $R^4$ is methyl and $R^5$ is hydrogen.

In one exemplification of the invention, W is $R^1SO_2$ and A is Radical II (in which both configurations of the trans radical are contemplated within the scope of this invention). Specific embodiments of this class include (note that the methyl group is conventionally indicated as a single bond attached to a ring):

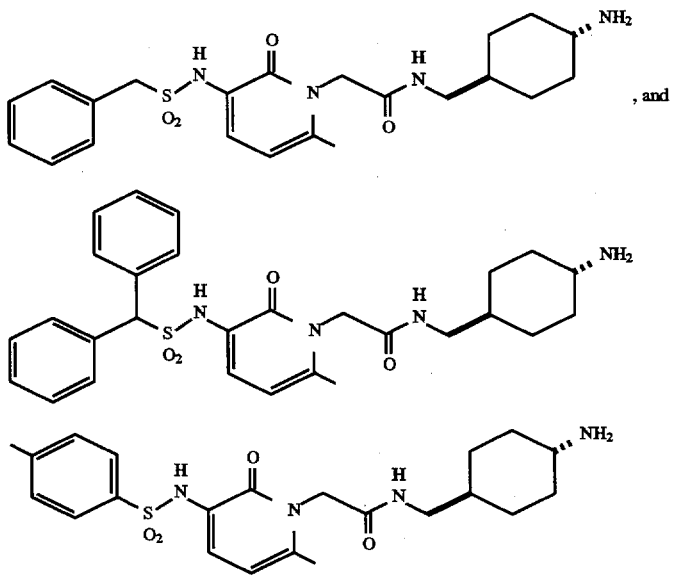

In another exemplification of the invention, W is $R^1SO_2$ and A is Radical III. Specific embodiments of this class include:

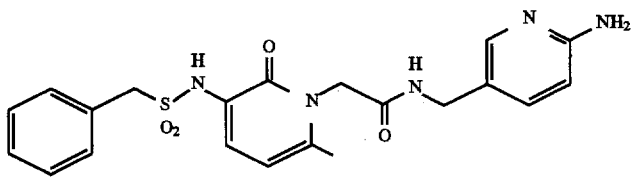
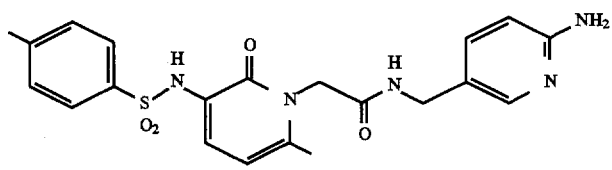
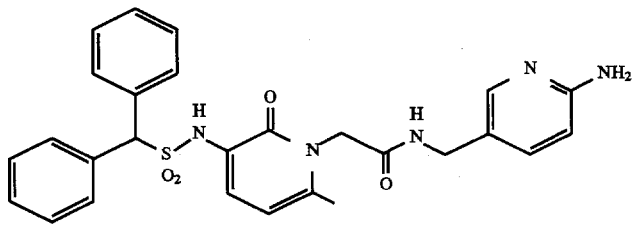
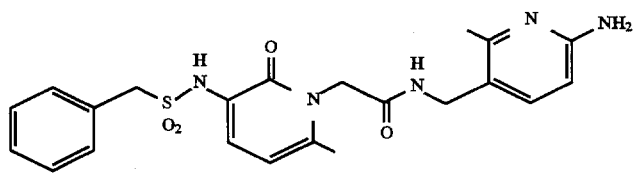
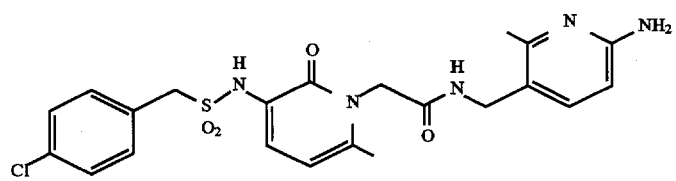
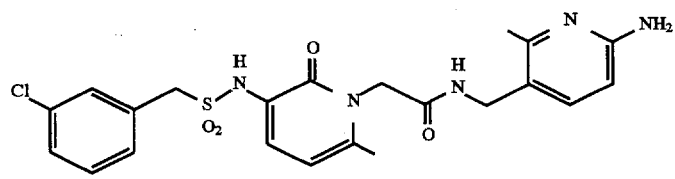
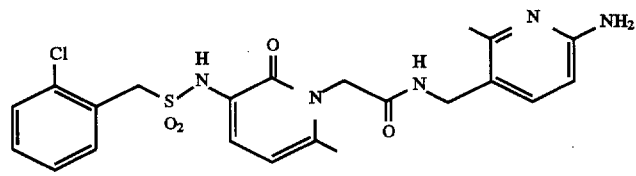
In a third exemplification of the invention, W is $R^1SO_2$ and A is Radical IV. Specific embodiments of this class include:
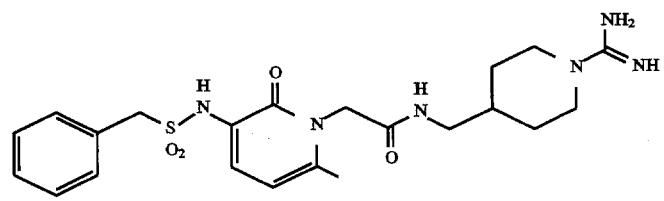

-continued

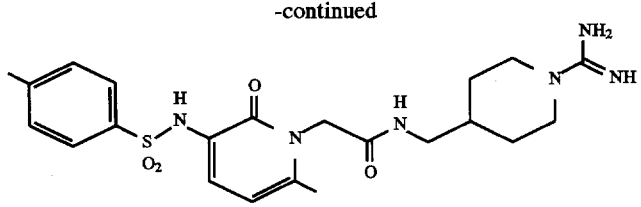

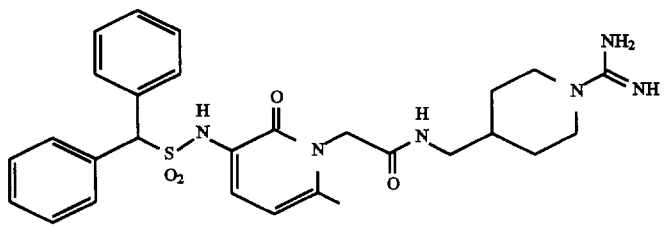

The compounds of the present invention, may have chiral centers and occur as racemates, racemic mixtures and as individual diastereomers, or enantiomers with all isomeric forms being included in the present invention. A racemate or racemic mixture does not imply a 50:50 mixture of stereoisomers.

When any variable occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "$C_{3-7}$cycloalkyl" is intended to include cyclopropyl, cyclobutyl, cyclopentyl, cyclohexyl and cycloheptyl, and the like.

The term "$C_{7-12}$ bicyclic alkyl" is intended to include bicyclo[2.2.1]heptyl (norbornyl), bicyclo[2.2.2]octyl, 1,1,3-trimethyl-bicyclo[2.2.2]heptyl (bornyl), and the like.

The term "heterocycle" or "heterocyclic ring", as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Thrombin inhibitors—therapeutic uses and methods of using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethylaspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.1 mg per kg of body weight per day (mg/kg/day) to about 100 mg/kg/day and preferably 1.0–100 mg/kg/day and most preferably 1–20 mg/kg/day. Intravenously, the most preferred doses will range from about 0.01 to about 10 mg/kg/minute during a constant rate infusion. Advantageously, the thrombin inhibitors may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The thrombin inhibitors can also be co-administered with suitable anti-coagulation agents or thrombolytic agents such as plasminogen activators or streptokinase to achieve synergistic effects in the treatment of various ascular pathologies. For example, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter. They may also be combined with heparin, aspirin, or warfarin.

Methods of making

The following synthetic Methods A to E can be used to prepare the compounds of the present invention.

Two methods for preparing compounds which contain radical IV as an end group are illustrated as Methods A and B and are exemplified by Examples I and XXV.

METHOD A

As exemplified by Example 1, methyl-2-hydroxy-6-methylpyridinone-3-carboxylate is alkylated with t-butylbromoacetate using a base such as cesium carbonate in DMF, or sodium hydride in THF. The t-butyl group is removed using a strong acid such as HCl gas and the amide of 4-aminomethyl-1-t-butoxycarbonylpiperidine is made using a standard coupling procedure. The methyl ester is hydrolyzed with lithium hydroxide and then a Curtius rearrangement (with acyl azide formation using DPPA and triethylamine as the base) gives the isocyanate which is trapped with benzyl alcohol in the presence of triethylamine giving the Cbz protected aminopyridinone. The Cbz group is removed by hydrogenolysis using Pearlman's catalyst under standard conditions. Bis-benzylsulfonylation can be accomplished using benzylsulfonyl chloride and triethylamine in methylene chloride. The BOC group is removed using a strong acid such as HCl gas and amidinopiperidine formation can be performed using an amidine transfer reagent such as aminoiminomethanesulfonic acid with triethylamine as a base in DMF. One of the sulfonyl groups is then removed using aqueous lithium hydroxide.

Amide couplings, e.g., Step D in Method A, to form the compounds of this invention can be performed by the carbodiimide method with reagents such as dicyclohexylcarbodiimide, or 1-ethyl-3-(3-dimethylaminopropyl) carbodiimide. Other methods of forming the amide or peptide bond include, but are not limited to the synthetic routes via an acid chloride, azide, mixed anhydride or activated ester. Typically, solution phase amide couplings are performed, but solid-phase synthesis by classical Merrifield techniques may be employed instead. The addition and removal of one or more protecting groups is also typical practice.

Modifications of Methods A to E will allow different W, A and $R^3$ groups contemplated by the scope of the broad claim below to be present by the use of an appropriate reagent or appropriately substituted starting material in the indicated synthetic step. For example, in the following Method A, the starting pyridine in Step A, can have as the 6-substituent, ethyl, isopropyl, cyclopropyl, and the like, to achieve the different operable values of $R^3$. Likewise, different W groups can be present by the use of an appropriate alkylating, carbonylating, sulfonylating, urealating agent, and the like, in Step H. Use of, for example, an alkyl halide, alkoxycarbonyl halide, acyl halide, alkylsulfonyl halide, or alkyl isocyanate will yield the corresponding values of W where W is $R^1$, $R^1OCO$, $R^1CO$, $R^1SO_2$, or $(R^1)_m(CH_2)_nNCO$. Likewise, the different Radicals A can be present by the appropriate choice of the radical precursor in Step D. Obvious variations and modifications of the Methods to produce similar and obvious variants thereof, will be apparent to one skilled in the art.

METHOD A

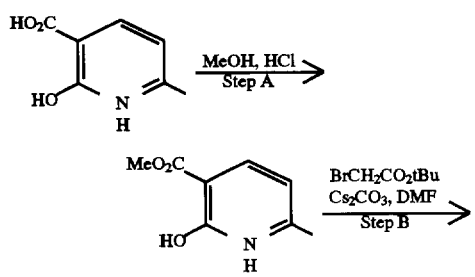

-continued
METHOD A

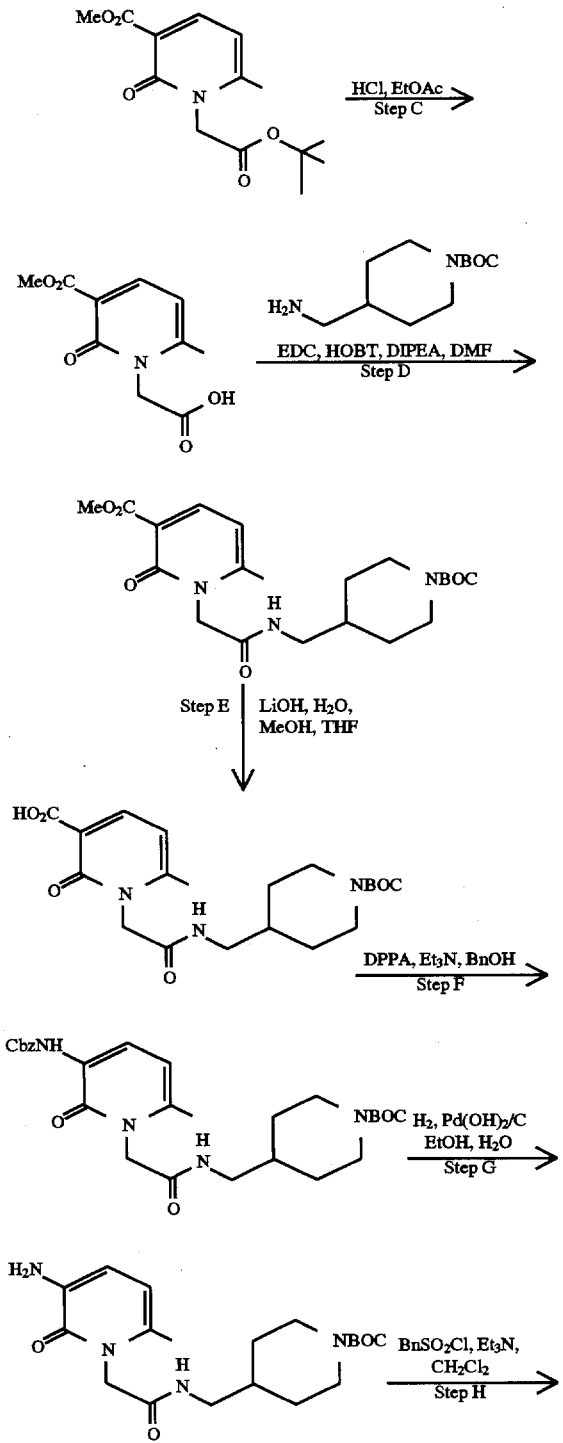

METHOD A
-continued

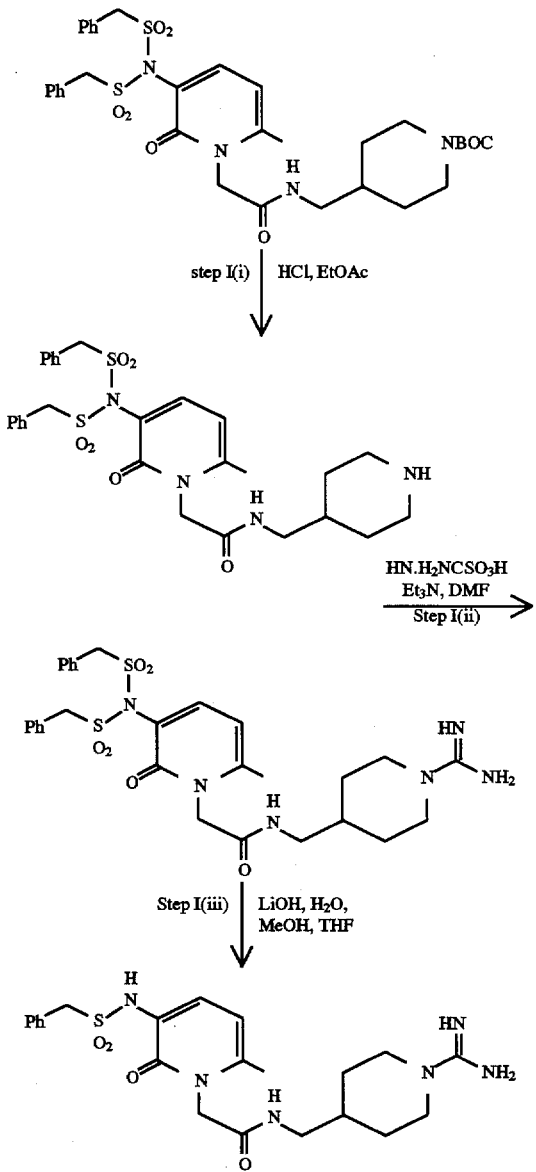

METHOD B

Following Method B below, starting 6-methyl-2-hydroxypyridine carboxylic acid is reacted with diphenylphosphoryl azide (DPPA) and benzyl alcohol in Step A to afford the protected pyridinone. This is alkylated with a glycine equivalent in Step B such as t-butylbromoacetate using a base such as cesium carbonate or sodium hydride. The t-butyl group is removed using a strong acid such as HCl gas in Step C and the amide of 4-aminomethyl-1-t-butoxycarbonylpiperidine is made using a standard coupling procedure in Step D. The CBZ group is removed in Step E via hydrogenation over a catalyst. The resulting amine is then reacted with the appropriate reagent, in this case benzylsulfonyl chloride, in Step F with pyridine as an acid scavenger and the BOC group is then removed in Step G using a strong acid such as HCl gas. Amidinopiperidine formation can be performed using an amidine transfer reagent such as aminoiminomethanesulfonic acid with triethylamine as a base in DMF. Alternatively the product of step G can be reacted with cyanogen bromide to give the cyanamide in Step H which can be further reacted with hydroxylamine to give the hydroxyguanidine.

Modifications of Method B will allow different W, A and $R^3$ groups contemplated by the scope of the broad claim below to be present by the use of an appropriate reagent or appropriately substituted starting material in the indicated synthetic step. For example, in the following Method B, the starting pyridine in Step A, can have as the 6-substituent, ethyl, isopropyl, cyclopropyl, and the like, to achieve the different operable values of $R^3$. Likewise, different W groups can be present by the use of an appropriate alkylating, carbonylating, sulfonylating, urealating agent, and the like, in Step F. Use of, for example, an alkyl halide, alkoxycarbonyl halide, acyl halide, alkylsulfonyl halide, or alkyl isocyanate will yield the corresponding values of W where W is $R^1$, $R^1OCO$, $R^1CO$, $R^1SO_2$, or $(R^1)_m(CH_2)_n NCO$. Likewise, the different Radicals A can be present by the appropriate choice of the radical precursor in Step D. Obvious variations and modifications of the Method to produce similar and obvious variants thereof, will be apparent to one skilled in the art.

Method B

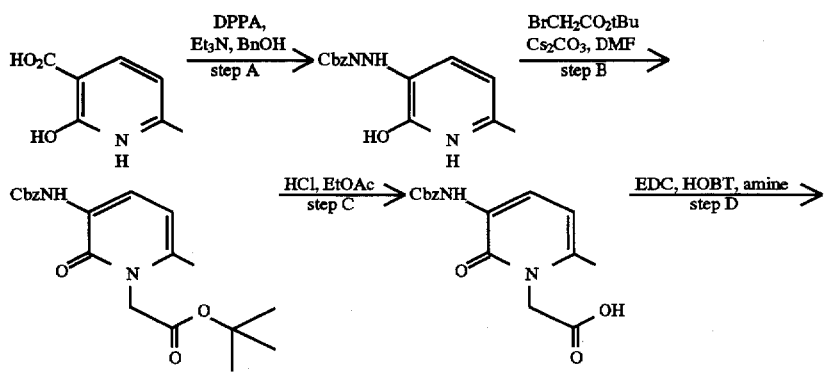

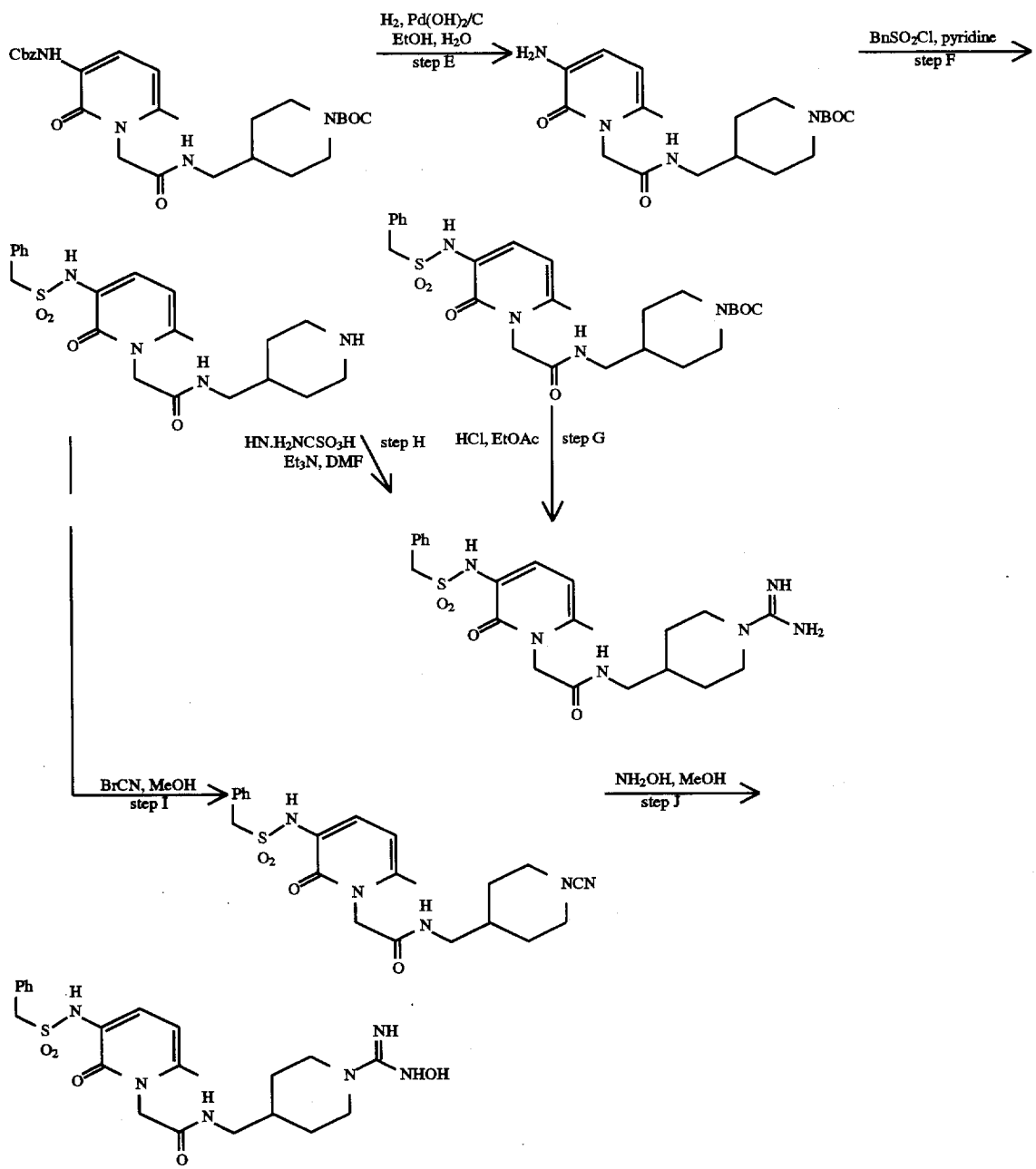

METHOD C

For preparing compounds which contain radical II as an end group one can use the following illustrated Method C. As exemplified by Example II, 2-hydroxy-3-nitro-6-methylpyridine is alkylated with ethylbromoacetate. The methyl ester is hydrolyzed with lithium hydroxide and the amide of trans-4-t-butoxycarbonylaminocyclohexylmethylamine is made using a standard coupling procedure. The nitro group is reduced by hydrogenation using a palladium catalyst under standard conditions. The amino group is alkylated by reduction with sodium triacetoxyborohydride of the imine formed from phenylacetaldehyde. The BOC group is removed using a strong acid such as HCl gas.

Modifications of Method C will allow different W, A and $R^3$ groups contemplated by the scope of the broad claim below to be present by the use of an appropriate reagent or appropriately substituted starting material in the indicated synthetic step. For example, in the following Method C, the starting pyridine in Step A, can have as the 6-substituent, ethyl, isopropyl, cyclopropyl, and the like, to achieve the different operable values of $R^3$. Likewise, different W groups can be present by the use of an appropriate alkylating, carbonylating, sulfonylating, urealyting agent, and the like, in Step E. Use of, for example, an alkyl aldehyde, alkyl halide, alkoxycarbonyl halide, acyl halide, alkylsulfonyl halide, or alkyl isocyanate will yield the corresponding values of W where W is $R^1$, $R^1OCO$, $R^1CO$, $R^1SO_2$, or $(R^1)m(CH_2)_nNCO$. Likewise, the different Radicals A can be present by the appropriate choice of the radical precursor in Step C. Obvious variations and modifications of the Methods to produce similar and obvious variants thereof, will be apparent to one skilled in the art.

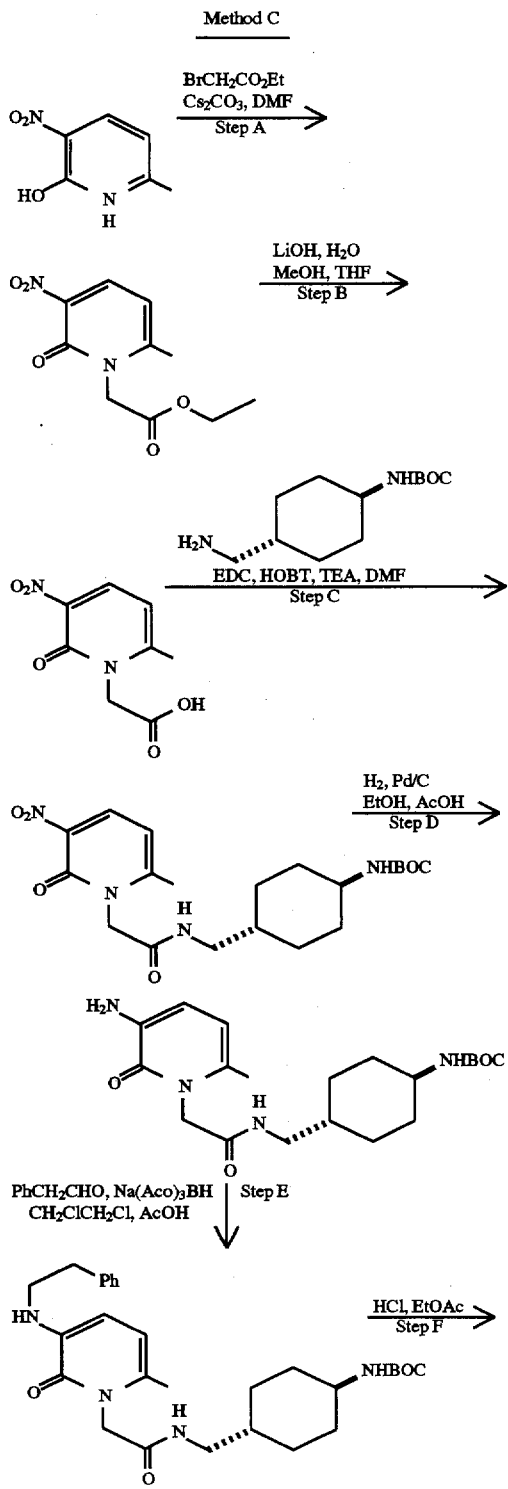

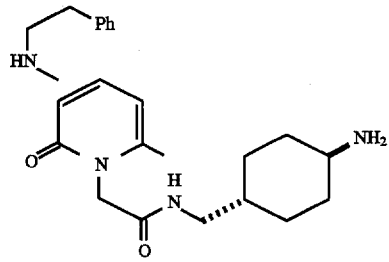

METHOD D

A method for preparing compounds which contain radical III is illustrated by following Method D and is exemplified by Example V. In Step A the CBZ group is removed from the product of Method B, Step B via hydrogenation over a catalyst. The resulting amine is then reacted with the appropriate reagent, in this case benzylsulfonyl chloride, in Step B with pyridine as an acid scavenger and the t-butyl ester is then removed under acidic conditions in Step C. The acid is then coupled in Step D with an amine, such as 2-t-butoxycarbonylamino-6-methyl-5-aminomethyl pyridine and the BOC group is removed in Step E with a strong acid.

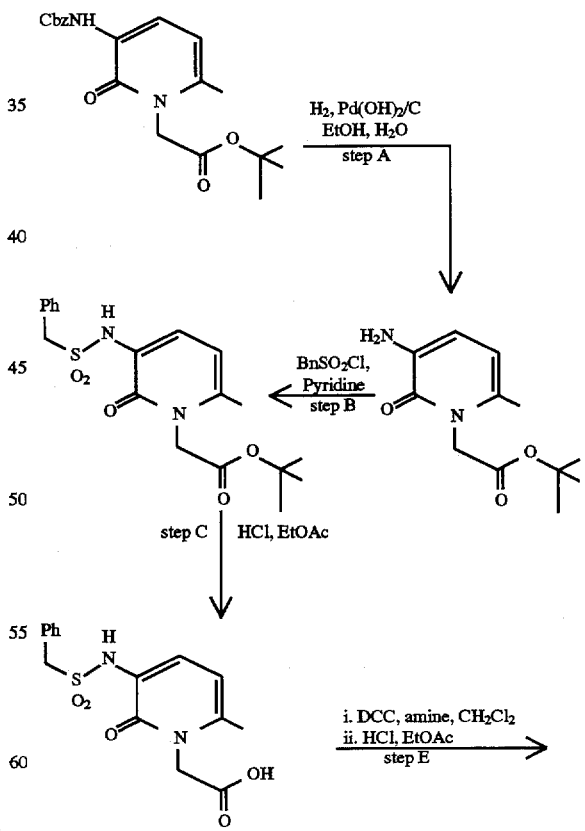

-continued
Method D

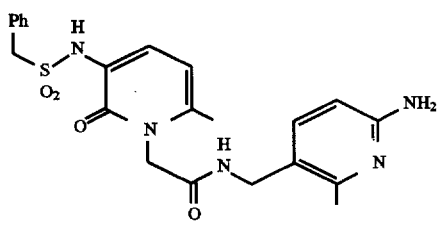

Modifications of Method D will allow different W, A and R³ groups contemplated by the scope of the broad claim below to be present by the use of an appropriate reagent or appropriately substituted starting material in the indicated synthetic step. For example, the starting pyridinone in Step A, can have as the 6-substituent, ethyl, isopropyl, cyclopropyl, and the like, to achieve the different operable values of $R^3$. Likewise, different W groups can be present by the use of an appropriate alkylating, carbonylating, sulfonylating, urealyting agent, and the like, in Step B. Use of, for example, an alkyl halide, alkoxycarbonyl halide, acyl halide, alkylsulfonyl halide, or alkyl isocyanate will yield the corresponding values of W where W is $R^1$, $R^1OCO$, $R^1CO$, $R^1SO_2$, or $(R^1)_m(CH_2)_nNCO$. Likewise, the different substituted Radicals IV can be present by the appropriate choice of the substituted radical precursor in Step D. Obvious variations and modifications of the Methods to produce similar and obvious variants thereof, will be apparent to one skilled in the art.

METHOD E

For preparing compounds which contain a 6-trifluoromethylpyridinone, one can use the following illustrated Method E. As exemplified by Example XXIII, starting butyl-2-trifluoroacetylvinyl ether is condensed with nitroacetamide in the presence of a base such as sodium ethoxide in Step A. The resulting pyridinone is allylated using π-allyl palladium in Step B and the nitro-group is reduced in Step C. The amine is then reacted with the appropriate reagent, in this case benzylsulfonyl chloride, in Step D with pyridine as an acid scavenger. The olefin is oxidatively cleaved to give the aldehyde which is further oxidised to the acid in Step E. The acid is then coupled in Step F with an amine, such as 2-t-butoxycarbonylamino-6-methyl-5-aminomethyl pyridine and the BOC group is removed with a strong acid.

Method E

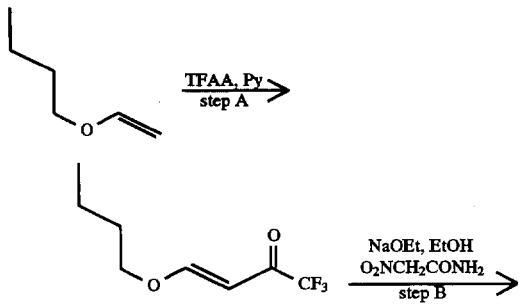

-continued
Method E

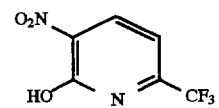

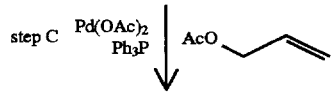

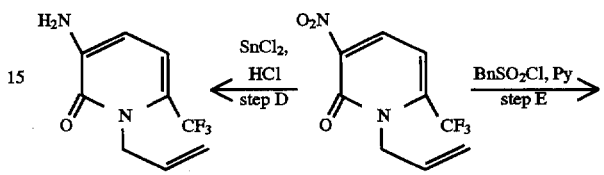

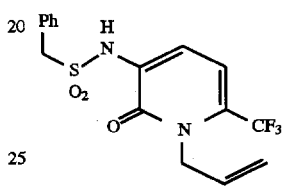

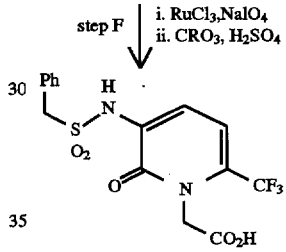

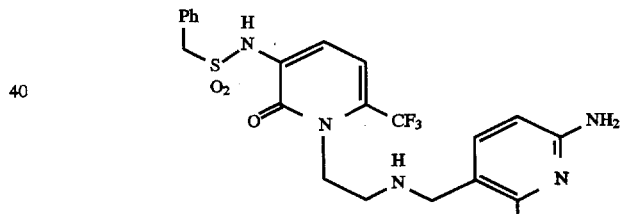

Modifications of Method E will allow different W and A groups contemplated by the scope of the broad claim below to be present by the use of an appropriate reagent or appropriately substituted starting material in the indicated synthetic step. For example, different W groups can be present by the use of an appropriate alkylating, carbonylating, sulfonylating, urealyting agent, and the like, in Step E. Use of, for example, an alkyl halide, alkoxycarbonyl halide, acyl halide, alkylsulfonyl halide, or alkyl isocyanate will yield the corresponding values of W where W is $R^1$, $R^1OCO$, $R^1CO$, $R^1SO_2$, or $(R^1)_m(CH_2)_nNCO$. Likewise, the different substituted Radicals A can be present by the appropriate choice of the substituted radical precursor in Step G. Obvious variations and modifications of the Method to produce similar and obvious variants thereof, will be apparent to one skilled in the art.

The following examples are illustrative of the invention as contemplated by the inventors and should not be construed as being limits on the scope or spirit of the instant invention.

Note that the NMR field strength employed in the below given examples was either 300 or 400 MHz.

EXAMPLE 1

Preparation of 3-Benzylsulfonylamino-6-methyl-1-(4-methylene-carboxamidomethyl-1-amidinopiperidinyl)-2-pyridinone Lithium hydroxide (8.23 ml of 1 M aqueous solution) was added to a stirred solution of methyl-6-methyl-1-(4-methylenecarboxamidomethyl-1-t-butoxycarbonylpiperidinyl)-2-pyridinone-3-carboxylate

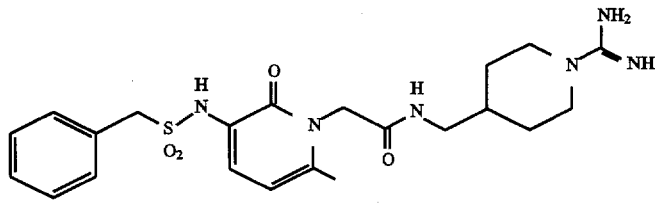

Step A: Methyl-2-hydroxy-6-methylpyridine-3-carboxylate

Acetyl chloride (50 ml) was added cautiously to a stirred suspension of 2-hydroxy-6-methylpyridine-3-carboxylic acid (14.3 g, 93.44 mmol) in dry methanol (500 ml) and the resulting solution was heated to reflux. After 16 h the solution was evaporated in vacuo to give the title compound (15.62 g, 100%) as a solid: $^1$H NMR (DMSO) shows the methyl singlet at δ3.71.

Step B: Methyl-6-methyl-1(t-butyl-methylenecarboxy)-2-pyridinone-3-carboxylate t-Butylbromoacetate (13.8 ml, 93.46 mmol) was added to a stirred suspension of methyl-2-hydroxy-6-methylpyridine-3-carboxylate (15.62 g, 93.44 mol) and cesium carbonate (30.44 g, 93.43 mmol) in dry DMF (180 ml). After 64 h, the reaction was evaporated in vacuo to a thick paste which was partitioned between ethyl acetate and brine, adding enough water to dissolve all the salts. The organic layer was dried ($Na_2SO_4$) and evaporated in vacuo. The resulting material was purified by flash column chromatography on silica (ethyl acetate/hexanes gradient, 30–50% ethyl acetate) to give the title compound (8.2 g, 31 %) as a foam: $^1$H MR ($CDCl_3$) δ1.48 (s, 9 H), 2.35 (s, 3 H), 3.88 (s, 3 H), 4.76 (s, 2 H), 6.14 (d, J=7.5 Hz, 1H), 8.12 (d, J=7.5 Hz, 1H).

Step C: Methyl-6-methyl-1-methylenecarboxy-2-pyridinone-3-carboxylate

HCl gas was bubbled through a stirred solution of methyl-6-methyl-1(t-butyl-methylenecarboxy)-2-pyridinone-3-carboxylate (8.2 g, 29.1 mmol) in ethyl acetate/methylene chloride (40 ml) at 0° C. for 10 min. After 1 hour, the solution was warmed to RT and after a further 45 min the solution was degassed with argon and was evaporated in vacuo to give the title compound (6.37 g, 73%) as a solid: $^1$H NMR ($CDCl_3$) δ2.28 (s, 3H), 3.72 (s, 3H), 4.69 (s, 2H), 6.12 (d, J=7.5Hz, 1H), 8.13 (d, J=7.5Hz, 1H).

Step D: Methyl-6-methyl-1-(4-methylenecarboxamidomethyl-1-t-butoxycarbonylpiperidinyl)-2-pyridinone-3-carboxylate EDC hydrochloride (2.34 g, 12.18 mmol) was added to a stirred mixture of methyl-6-methyl-1-methylenecarboxy-2-pyridinone-3-carboxylate (2.0 g, 8.88 mmol), 4-aminomethyl-1-t-butoxycarbonyl-piperidine (3.0 g, 14.21 mmol), HOBT (1.65 g, 12.18 mmol) and diisopropylethylamine (3.6 ml, 10.30 mmol) in dry DMF (20 ml). After 16 h the reaction was diluted with ethyl acetate and was washed with 10% citric acid solution, water, saturated sodium hydrogen carbonate solution and brine, dried ($MgSO_4$) and evaporated in vacuo to give the title compound (3.0 g, 80%) as a foam: $^1$H NMR ($CDCl_3$) selected signals at δ1.44 (s, 9H, t-Bu), 3.89 (s, 3H, OMe), 7.11 (br t, J=5.3Hz, 1H, NH).

Step E: 6-Methyl-1-(4-methylenecarboxamidomethyl-1-t-butoxy-carbonylpiperidinyl)-2-pyridinone-3-carboxylic acid (2.31 g, 5.48 mmol) in 1:1 methanol/THF (16 ml). After 16 h the reaction was concentrated in vacuo to remove the volatiles, and the resulting mixture was partitioned between ethyl acetate and 10% citric acid solution. The organic layer was washed with brine, dried ($MgSO_4$) and evaporated in vacuo to give the title compound (2.0 g, 90%) as a foam: $^1$H NMR ($CDCl_3$) shows loss of the methyl singlet at δ3.89.

Step F: 3-Benzyloxycarbonylamino-6-methyl-1-(4-methylene-carboxamidomethyl-1-t-butoxycarbonylpiperidinyl)-2-pyridinone DPPA (1.53 ml, 7.11 mmol) was added to a stirred solution of 6-methyl-1-(4-methylenecarboxamidomethyl-1-t-butoxycarbonyl-piperidinyl)-2-pyridinone-3-carboxylic acid (1.93 g, 4.74 mmol) and triethylamine (0.99 ml, 7.11 mmol) in dry dioxane (10 ml) and the resulting solution was heated to reflux. After 48 h more triethylamine (0.99 ml, 7.11 mmol) and benzyl alcohol (0.74 ml, 7.11 mmol) were added and the solution was refluxed for a further 24 h. The reaction was partitioned between ethyl acetate and 10% citric acid, and the organic layer was washed with water, sodium hydrogen carbonate solution and brine, dried ($MgSO_4$) and evaporated in vacuo to a foam. The crude product was purified by flash column chromatography (80% ethyl acetatelhexanes) to give the title compound (1.53 g, 63%) as a foam: $^1$H NMR ($CDCl_3$) selected signals at δ5.21 (s, 2H, $PhCH_2$), 7.33–7.41 (m, 5H, Ph), 7.69 (br s, 1H, CbzNH).

Step G: 3-Amino-6-methyl-1-(4-methylenecarboxamidomethyl-1-t-butoxycarbonylpiperidinyl)-2-pyridinone A mixture of 3-Benzyloxycarbonylamino-6-methyl-1-(4-methylenecarboxamidomethyl-1-t-butoxycarbonylpiperidinyl)-2-pyridinone (0.50 g, 0.975 mmol) and Pearlman's catalyst (200 mg) in 5:1 ethanol/water (60 ml) was stirred under $H_2$ (balloon) for 16 h. The reaction mixture was filtered through celite and evaporated in vacuo to give the title compound (0.385 g) as a foam: $^1$H NMR ($CDCl_3$) see disappearance of the Cbz protons. Selected signals at δ5.99 (d J=7.3 Hz, 1H, pyridinone H-5), 6.54 (d, J=7.3Hz, 1H, pyridinone H-4).

Step H: 3-N,N-(Bis-benzylsulfonyl)amino-6-methyl-1-(4-methylenecarboxamidomethyl-1-t-butoxycarbonylpiperidinyl)-2-pyridinone Benzylsulfonyl chloride (51 mg, 0.27 mmol) was added to a stirred solution of 3-amino-6-methyl-1-(4-methylenecarboxamidomethyl-1-t-butoxycarbonylpiperidinyl)-2-pyridinone (68 mg, 0.18 mmol) and triethylamine (0.075 ml, 0.54 mmol) in dry methylene chloride (0.5 ml). After 16 h the reaction was loaded directly onto silica and was purified by flash column chromatography (80% ethyl acetate/hexanes) to give the title compound (30 mg, 24%) as a foam: $^1$H NMR ($CDCl_3$)

selected signals at δ4.69 (s, 2 H, CH₂CO), 4.71 (d, J=13.7Hz, 2H, PhCHAHB), 5.17 (d, J=13.7Hz, 2H, PhCHAHB), 5.80 (coalescing AB system, 2H, pyridinone H's), 7.40–7.49 (m, 1OH, Ph's).

Step I: 3-Benzylsulfonylamino-6-methyl-1-(4-methylenecarboxamidomethyl-1-amidinopiperidinvl)-2-pyridinone HCl Gas was bubbled through a solution of 3-N,N-(Bis-benzylsulfonyl)amino-6-methyl-1-(4-methylenecarboxamidomethyl-1-t-butoxycarbonylpiperidinyl)-2-pyridinone (30 mg, 0.044 mmol) in 1:1 methylene chloride/ethyl acetate (2 ml) for 5 min at 0° C. After a further 1 h the solution was degassed with argon and was evaporated in vacuo to a glass. The resulting material was dissolved in DMF (0.5 ml) and aminoiminomethanesulfonic acid (11 mg) and triethylamine (0.025 ml) were added. After 48 h the reaction was evaporated in vacuo and then was dissolved in 1:1 methanol/THF (2 ml) and 1 M LiOH (1 ml) was added. After 3 h the reaction was concentrated in vacuo and the crude product purified by preparative HPLC (C₁₈, 0.1% TFA/H₂O,CH₃CN gradient) to give the title compound (15.9 mg, 61%) as a glass: ¹H NMR (CD₃OD) δ1.25 (m, 2 H), 1.84 (m, 3H), 2.33 (s, 3H), 3.04 (m, 2H), 3.16 (m, 2H), 3.87 (br d, J=13.7Hz, 2H), 4.45 (s, 2H), 4.79 (s, 2 H), 6.15 (d, J=7.5Hz, 1H), 7.28–7.32 (m, 6H), 8.34 (br m, 1H); MS (FAB) 475 (M+1)⁺.

EXAMPLE II

Preparation of 3-(2-Phenylethylamino)-6-methyl-1-(methylenecarboxamido-trans-4-aminocyclohexylmethyl)-2-pyridinone

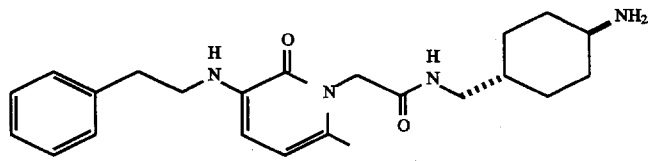

Step A: 3-Nitro-6-methyl-1(ethyl-methylenecarboxy)-2-pyridinone

Ethylbromoacetate (0.61 ml, 5.5 mmol) was added to a stirred suspension of 3-nitro-2-hydroxy-6-methylpyridine (0.77 g, 5.0 mmol) and cesium carbonate (1.63 g, 5.0 mmol) in dry DMF (10 ml). After 16 h, the reaction was acidified with 1 M HCl and was extracted into ethyl acetate, washed with sodium hydrogen carbonate solution and brine, dried (Na₂SO₄) and evaporated in vacuo to a gum. The crude product was purified by flash column chromatography on silica (ethyl acetate/hexanes gradient, 20–70% ethyl acetate) to give the title compound (0.45 g, 37%) as a foam: ¹H NMR (CDCl₃) δ1.31 (t, J=7.1Hz, 3H), 2.44 (s, 3H), 4.26 (q, J=7.1 Hz, 2H), 4.88 (s, 2H), 6.22 (d, J=7.9Hz, 1H), 8.33 (d, J=7.9Hz, 1H).

Step B: 3-Nitro-6-methyl-1-methylenecarboxy-2-pyridinone

Lithium hydroxide (86 mg, 2.05 mmol) was added to a stirred solution of 3-Nitro-6-methyl-1(ethyl-methylenecarboxy)-2-pyridinone (0.45 g, 1.86 minmol) in 1:1:1 methanol/THF/water (6 ml). After 64 h the reaction was diluted with sodium hydrogen carbonate solution and was washed with methylene chloride (3 times). The aqueous layer was acidified with concentrated HCl to pH 1 and was concentrated in vacuo to the point when sodium chloride started to crystallize from the solution. The mixture was then extracted with ethyl acetate (3 times) and the combined extracts were dried (Na₂SO₄) and evaporated in vacuo to give the title compound (285 mg, 72%) as a tan solid: ¹H NMR (CD₃OD) shows loss of the ethyl signals.

Step C: 3-Nitro-6-methyl-1-(methylenecarboxamido-trans-4-t-butoxycarbonylaminocyclohexylmethyl)-2-pyridinone EDC hydrochloride (249 mg, 1.30 mmol) was added to a stirred mixture of 3-nitro-6-methyl-1-methylenecarboxy-2-pyridinone (212 mg, 1.00 mmol), trans-4-t-butoxycarbonylaminocyclohexylmethyl-amine (228 mg, 1.00 mmol), HOBT (176 mg, 1.30 mmol) and triethylamine (0.18 ml, 1.30 mmol) in dry DMF (4 ml). After 16 h the reaction was diluted with ethyl acetate and was washed with 5% KHSO₄ solution, saturated sodium hydrogen carbonate solution and brine, dried (MgSO₄) and evaporated in vacuo to a solid. The crude product was purified by flash column chromatography on silica (ethyl acetate/hexanes gradient, 20–40% ethyl acetate) to give the title compound (280 mg, 66%) as a solid: ¹H NMR (CDCl₃) selected signals at δ1.43 (s, 9H, t-Bu), 3.08 (t, J=6.4Hz, 2H, NHCH₂), 3.34 (br s, 1H, BOCNHCH, 4.35 (br s, 1H, BOCNH), 6.79 (br t, 1H, NHCH₂).

Step D: 3-Amino-6-methyl-1-(methylenecarboxamido-trans-4-t-butoxycarbonylaminocyclohexylmethyl)-2-pyridinone A mixture of 3-nitro-6-methyl-1-(methylenecarboxamido-trans-4-t-butoxycarbonylaminocyclohexylmethyl)-2-pyridinone (280 mg, 0.66 mmol) and 10% palladium on carbon (29 mg) in 10:1 ethanol acetic acid (11 ml) was stirred under hydrogen (balloon) for 16 h. The mixture was filtered through celite and evaporated in vacuo to a semi-solid. The crude product was purified by flash column chromatography on silica (ethyl acetate/hexanes gradient, 70–100% ethyl acetate followed by a chloroform/methanol gradient, 2–8% methanol) to give the title compound (159 mg, 61 %) as a pale tan solid: ¹H NMR (CDCl₃) selected signals at δ4.33 (br s, 1H, NH₂), 5.98 (d, J=7.3Hz, 1H), 6.53 (d, J=7.3Hz, 1H).

Step E: 3-(2-Phenylethylamino)-6-methyl-1-(methylenecarboxamido-trans-4-t-butoxycarbonylaminocyclohexylmethyl)-2-pyridinone Sodium triacetoxyborohydride (49 mg, 0.23 mmol) was added to a stirred solution of 3-amino-6-methyl-1-(methylene-carboxamido-trans-4-t-butoxycarbonylaminocyclo-hexylmethyl)-2-pyridinone (60 mg, 0.153 mmol) and phenyl acetaldehyde (0.020 ml, 0.17 mmol) in 0.24 M acetic acid in 1,2-dichloroethane (0.77 ml). After 16 h the mixture was quenched with water and extracted into ethyl acetate. The ethyl acetate layer was washed with sodium carbonate solution and brine, dried (Na₂SO₄) and evaporated in vacuo to a glass. The crude product was purified by flash column chromatography on silica (ethyl acetate/hexanes gradient, 20–70% ethyl acetate) to give the title compound (52.7 mg, 69%) as a solid: ¹H NMR (CDCl₃) selected signals at δ.94 (t, J=7.2Hz, 2H, PhCH₂), 3.03 (t, J=6.4Hz, 2H, CONHCH₂), 3.32 (q, J=7.2Hz, 2H, PhCH₂CH₂), 4.1 (br t, 1H, CH₂CH₂NH), 7.22–7.33 (m, 5H, Ph).

Step F: 3-(2-Phenylethylamino)-6-methyl-1-(methylenecarbox-amido-trans-4-aminocyclohexylmethyl)-2-pyridinone 3-(2-Phenylethylamino)-6-methyl-1-(methylenecarboxamido-trans-4-t-butoxycarbonylaminocyclohexylmethyl)-2-pyridinone (52.7 mg, 0.106 mmol) was dissolved in ethyl acetate saturated with HCl gas (5 ml). After 30 min the solution was evaporated in vacuo to a yellow solid. The crude product was purified by preparative HPLC ($C_{18}$, 0.1% TFA/$H_2O$, $CH_3CN$ gradient) to give the title compound (32.4 mg, 46%) as a wax: $^1$H NMR ($CD_3OD$) see disappearance of the BOC group; Anal. ($C_{23}H_{32}N_4O_2$·2.1 TFA·1.8 $H_2O$); HRMS (FAB) calc'd for $C_{23}H_{33}N_4O_2$ (M+1)+397.2604, found 397.2614.

EXAMPLE III

Preparation of 3-Benzylsulfonylamino-6-methyl-1-(methylenecarboxamido-trans-4-amino cyclohexylmethyl)-2-pyridinone

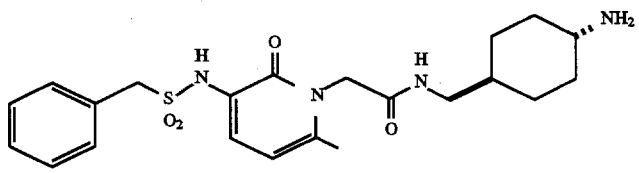

Step A: 3-Benzylsulfonylamino-6-methyl-1-(methylenecarboxamido-trans-4-t-butyloxycarbonyl-amino-cyclohexylmethyl)-2-pyridinone EDC hydrochloride (50 mg, 0.260 mmol) was added to a stirred mixture of 3-benzylsulfonylamino-6-methyl-1-methylenecarboxy-2-pyridinone (73 mg, 0.217 mmol), trans-4-t-butoxycarbonylaminocyclohexylmethylamine (51 mg, 0.260 mmol), HOBT (35 mg, 0.260 mmol) and triethylamine (0.073 ml, 0.521 mmol) in dry DMF (3 ml). After 3 d the reaction was diluted with ethyl acetate and was washed with water (100 ml), and brine, dried ($MgSO_4$) and evaporated in vacuo to give the title compound: $^1$H NMR ($CDCl_3$) selected signals at δ1.44 (s, 9H, t-Bu), 2.44 (s, 3H), 3.09 (t, J=6.3 Hz, 2H, $NHCH_2$), 3.34 (br s, 1H, NH), 4.30 (s, 2H), 4.55 (s, 2H), 6.05 (d, J=7.7 Hz, 1H), 6.79 (br t, NH), 7.23–7.27 (m, 5H), 7.34 (d, J =7.7 Hz, 1H).

Step B: 3-Benzylsulfonylamino-6-methyl-1-(methylenecarboxamido-trans-4-aminocyclohexylmethyl)-2-pyridinone HCl Gas was bubbled through a solution of 3-benzylsulfonylamino-6-methyl-1-(methylenecarboxamido-trans-4-t-butoxycarbonylaminocyclohexylmethyl)-2-pyridinone (118.6 mg, 0.217 mmol) in ethyl acetate (20 ml) for 5 min at 0° C. After 0.5 hour the solution was degassed with argon and evaporated in vacuo. The crude product was triturated with ethyl acetate to give the title compound (80.1 mg) as a solid, m.p.>200° C.: $^1$H NMR ($CD_3OD$) see disappearance of the BOC group; HRMS (FAB) calc'd for $C_{22}H_{31}N_4O_4S$ (M+1)+ 447.2066, found 447.2048.

EXAMPLE IV

Preparation of 3-Benzylsulfonylamino-6-methyl-1-(2-amino-5-methylenecarboxamidomethylpyridinyl)-2-pyridinone

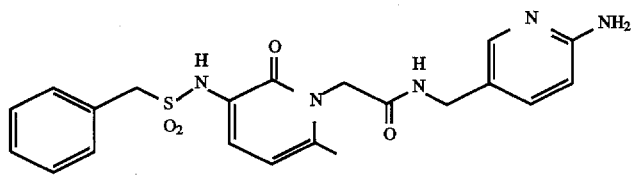

Step A: 3-Benzyloxycarbonylamino-6-methyl-2-pyridinone

DPPA (35.6 ml, 165 mmol) was added to a stirred solution of 2-hydroxy-6-methylpyridine-3-carboxylic acid (22.97 g, 150 mmol) and triethylamine (23.0 ml, 165 mmol) in dry dioxane (300 ml) and the resulting solution was heated to reflux. After 16 h more triethylamine (23.0 ml, 165 mmol) and benzyl alcohol (17.1 ml, 150 mmol) were added and the solution was refluxed for a further 24 h. The reaction was concentrated in vacuo to remove most of the volatiles. The residue was partitioned between methylene chloride and brine, acidified to pH 1 with 1 M HCl. The organic layer was washed with sodium hydrogen carbonate solution and brine, dried ($MgSO_4$) and evaporated in vacuo. The crude product was purified by flash column chromatography (ethyl acetate/ hexanes gradient 70–80% ethyl acetate, followed by 5% methanol/chloroform). The resulting solid was recrystallized from methanol, to give the title compound (21.15 g, 55%): $^1$H NMR ($CDCl_3$) δ2.29 (s, 3H, $CH_3$), 5.20 (s, 2H, $PhCH_2$), 6.06 (d, J=7.6Hz, pyridinone-5-H), 7.32–7.43 (m, 5H, Ph), 7.67 (br s, 1H, CbzNH), 8.03 (br d, pyridinone-4-H).

Step B: 3-Benzyloxycarbonylamino-6-methyl-1-(t-butyl-methylenecarboxy)-2-pyridinone t-Butylbromoacetate (12.1 ml, 81.98 mmol) was added to a stirred suspension of 3-benzyloxycarbonylamino-6-methyl-2-pyridinone (21.15 g, 81.98 mmol) and cesium carbonate (26.71 g, 81.98 mmol) in dry DMF (170 ml). After 36 h, the reaction was evaporated in vacuo to a thick paste which was partitioned between ethyl acetate and water. The organic layer was washed with water (3 times) and brine, dried ($MgSO_4$) and evaporated in vacuo. The resulting material was purified by flash column chromatography on silica (20% ethyl acetate/hexanes) to give the title compound (15.00 g, 49%) as a crystalline solid: $^1$H NMR ($CDCl_3$) δ1.47 (s, 9 H), 2.25 (s, 3 H), 4.75 (s, 2 H), 5.19 (s, 2 H), 6.09 (d, J=7.8 Hz), 7.30–7.40 (m, 5 H), 7.75 (br s, 1 H), 7.94 (br d, 1 H).

Step C: 3-Amino-6-methyl-1-(t-butyl-methylenecarboxy)-$^2$- pyridinone

A mixture of 3-benzyloxycarbonylamino-6-methyl-1-(t-butyl-methylenecarboxy)-2-pyridinone (3.16 g, 8.48 mmol)

and Pearlman's catalyst (360 mg) in 4:1 ethanol/water (120 ml) was stirred under H₂ (balloon) for 16 h. The reaction mixture was filtered through celite and evaporated in vacuo, azeotroping with ethanol. The crude product was purified by flash column chromatography on silica (50% ethyl acetate/ hexanes) to give the title compound (1.58 g, 78%) as a foam: $^1$H NMR (CDCl₃) δ1.46 (s, 9H, t-Bu), 2.18 (s, 3H, Me), 4.02 (br s, 2H, NH₂), 4.74 (s, 2H, CH₂), 5.90 (d, J =7.3Hz, 1H, pyridinone H-5), 6.47 (d, J=7.3Hz, 1H, pyridinone H-4).

EXAMPLE 5

Preparation of 3-Benzylsulfonylamino-6-methyl-1-(2-amino-6-methyl-5-methylenecarboxamidomethylpyridinyl)-2-pyridinone

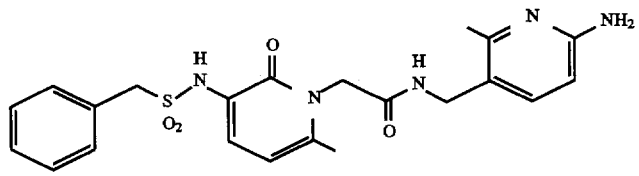

Step A: 3-Benzyloxycarbonylamino-6-methyl-2-pyridinone

DPPA (35.6 ml, 165 mmol) was added to a stirred solution of 2-hydroxy-6-methylpyridine-3-carboxylic acid (22.97 g, 165 mmol) and triethylamine (23.0 ml, 165 mmol) in dry dioxane (300 ml) and the resulting solution was heated to reflux. After 16 h more triethylamine (23.0 ml, 165 mmol) and benzyl alcohol (17.1 ml, 150 mmol) were added and the solution was refluxed for a further 24 h. The reaction was concentrated in vacuo to remove most of the volatiles. The residue was partitioned between methylene chloride (500 ml) and brine (500 ml), acidified to pH 1 with 1 M HCl (165 ml). The aqueous layer was extracted with methylene chloride (2 times) and the combined organic layers were washed with sodium hydrogen carbonate solution and brine, dried (Na₂SO₄) and evaporated in vacuo to a brown solid. This was recrystallized from methanol, to give the title compound (22.70 g, 59%) as a tan solid: $^1$H NMR (CDCl₃) δ2.29 (s, 3H, CH₃), 5.20 (s, 2 H, PhCH₂), 6.06 (d, J=7.6 Hz, pyridinone-5-H), 7.32–7.43 (m, 5 H, Ph), 7.67 (br s, 1 H, CbzNH), 8.03 (br d, pyridinone-4-H).

Step B: 3-Benzyloxycarbonylamino-6-methyl-1-(t-butyl-methylenecarboxy)-2-pyridinone t-Butylbromoacetate (12.98 ml, 87.89 mmol) was added to a stirred suspension of 3-benzyloxycarbonylamino-6-methyl-2-pyridinone (22.70 g, 87.89 mmol) and cesium carbonate (28.64 g, 87.89 mmol) in dry DMF (175 ml). After 16 h, the reaction was evaporated in vacuo to a thick paste which was partitioned between ethyl acetate and water. The organic layer was washed with water (3 times) and brine, dried (MgSO₄) and evaporated in vacuo to a solid. Hexanes (200 ml) was added to this material and the mixture was heated to reflux for 5 min, cooled and filtered, washing with cold hexanes to give the title compound (12.55 g, 38%) as a crystalline solid: $^1$H NMR (CDCl₃) δ1.47 (s, 9 H), 2.25 (s, 3 H), 4.75 (s, 2 H), 5.19 (s, 2 H), 6.09 (d, J=7.8 Hz), 7.30–7.40 (m, 5 H), 7.75 (br s, 1 H), 7.94 (br d, 1 H).

Step C: 3-Amino-6-methyl-1-(t-butyl-methylenecarboxy)-2-pyridinone

A mixture of 3-benzyloxycarbonylamino-6-methyl-1-(t-butyl-methylenecarboxy)-2-pyridinone (5.59 g, 15.0 mmol) and Pearlman's catalyst (0.56 g) in 4:1 ethanol/water (200 ml) was shaken in a Parr apparatus under H₂ (50 psi) for 2 h. The reaction mixture was filtered through celite and evaporated in vacuo, azeotroping with ethanol to give the title compound (3.55 g, 99%) as a solid: $^1$H NMR (CDCl₃) δ1.46 (s, 9 H, t-Bu), 2.18 (s, 3 H, Me), 4.02 (br s, 2 H, NH₂), 4.74 (s, 2 H, CH₂), 5.90 (d, J=7.3 Hz, 1 H, pyridinone H-5), 6.47 (d, J=7.3 Hz, 1 H, pyridinone H-4).

Step D: 3-Benzylsulfonylamino-6-methyl-1-(t-butyl-methylene-carboxy)-2-pyridinone Pyridine (6.26 ml) was added to a mixture of 3-amino-6-methyl-1-(t-butyl-methylenecarboxy)-2-pyridinone (1.49 g, 6.25 mmol) and benzylsulfonyl chloride (1.31 g, 6.88 mmol) at 0° C. and as the resulting solution was stirred a thick precipitate formed. More pyridine (3.13 ml) was added and the slurry was stirred for 1 h. The reaction was partitioned between ethyl acetate and water. The cloudy ethyl acetate layer was dried (Na₂SO₄) and was evaporated in vacuo to give the desired product (1.42 g) as a pale pink solid. More product (0.97 g as a pale yellow solid) was recovered by washing the drying agent and filtration apparatus with methylene chloride. The title compound (2.39 g, 97%) was thus obtained: $^1$H NMR (CDCl₃) δ1.51 (s, 9H, t-Bu), 2.26 (s, 3H, Me), 4.31 (s, 2H, PhCH₂), 4.75 (s, 2H, NCH₂), 6.01 (d, J=7.7Hz, 1H, pyridinone H-5), 7.22–7.34 (m, 7H, remaining H).

Step E: 3-Benzylsulfonylamino-6-methyl-1-methylenecarboxy-2-pyridinone

HCl gas was bubbled through a stirred suspension of 3-benzyl sulfonylamino-6-methyl-1-(t-butyl-methylenecarboxy)-2-pyridinone (1.42 g, 3.62 mmol) in ethyl acetate (15 ml) at 0° C. until a solution had formed which was saturated with HCl. After 1 h at RT a thick suspension had formed. The mixture was degassed with argon and filtered to give the title compound (0.865 g, 71 %) as a solid: $^1$H NMR (CD₃OD) δ2.32 (s, 3H, Me), 4.43 (s, 2H, PhCH₂), 4.89 (s, 2 H, NCH₂), 6.14 (d, J=7.7Hz, 1H, pyridinone H-5), 7.28–7.33 (m, 6H, remaining H).

Step F: 3-Benzylsulfonylamino-6-methyl-1-(2-amino-5-methylenecarboxamidomethylpyridinyl)-2-pyridinone EDC hydrochloride (34.2 mg, 0.178 mmol) was added to a stirred mixture of 3-benzylsulfonylamino-6-methyl-1-methylenecarboxy-2-pyridinone (50.0 mg, 0.149 mmol), 2-amino-4-methylaminopyridine (18.3 mg, 0.149 mmol), HOBT (24.1 mg, 0.178 mmol) and triethylamine (0.050 ml, 0.359 mmol) in dry DMF (1 ml). After 64 h the reaction was diluted with ethyl acetate and was washed with water, saturated sodium hydrogen carbonate solution, water and brine, dried (Na₂SO₄) and evaporated in vacuo to a solid. The crude product was purified by flash column chromatography on silica (methanol/chloroform gradient, 5–7% methanol),and the resulting material was further purified by preparative HPLC (C₁₈, H₂O/CH₃CN gradient) to give the title compound (14 mg, 21%) as a glass: $^1$H NMR (CD₃OD) δ2.33 (s, 3H), 3.35 (s, 2H), 4.32 (s, 2H), 4.44 (s, 2H), 4.81 (s, 2H), 6.16 (d, J=7.5Hz, 1H), 6.86 (d, J=8.8Hz, 1H), 7.26–7.33 (m, 6H), 7.78–7.81 (m, 2H); MS (FAB) 442 (M+1)⁺.

Step D: 3-Benzylsulfonylamino-6-methyl-1-(t-butyl-methylene-carboxy)-2-pyridinone Benzylsulfonyl chloride (3.146 g, 16.5 mmol) was added to a solution of 3-amino-6-methyl-1-(t-butyl-methylenecarboxy)-2-pyridinone (3.55 g, 14.9 mmol) in pyridine (30 ml) at 0° C. and as the resulting solution was stirred a thick precipitate formed. After 1 h the reaction mixture was evaporated in vacuo to a thick paste. This was partitioned between methylene chloride and 10% potassium hydrogen sulfate solution. The organic layer was dried ($Na_2SO_4$) and evaporated in vacuo to give the desired product (5.70 g, 97%) as a pale pink solid: $^1$H NMR ($CDCl_3$) δ1.51 (s, 9 H, t-Bu), 2.26 (s, 3 H, Me), 4.31 (s, 2 H, $PhCH_2$), 4.75 (s, 2 H, $NCH_2$), 6.01 (d, J=7.7 Hz, 1 H, pyridinone H-5), 7.22–7.34 (m, 7 H, remaining H).

Step E: 3-Benzylsulfonylamino-6-methyl-1-methylenecarboxy-2-pyridinone

HCl gas was bubbled through a stirred suspension of 3-benzylsulfonylamino-6-methyl-1-(t-butyl-methylenecarboxy)-2-pyridinone (5.70 g, 14.52 mmol) in ethyl acetate (60 ml) at 0° C. until a solution had formed which was saturated with HCl. After 1.5 h at RT a thick suspension had formed. The mixture was degassed with nitrogen and filtered to give the title compound (4.00 g, 82%) as a pale pink solid: $^1$H NMR (CD3OD) δ2.32 (s, 3 H, Me), 4.43 (s, 2 H, $PhCH_2$), 4.89 (s, 2 H, $NCH_2$), 6.14 (d, J=7.7 Hz, 1 H, pyridinone H-S), 7.28–7.33 (m, 6 H, remaining H).

Step F: 3-Benzylsulfonylamino-6-methyl-1-(2-amino-6-methyl-5-methvlenecarboxamidomethylpyridinyl)-2-pyridinone DCC (0.61 g, 2.98 mmol) was added to a stirred solution of 3-benzylsulfonylamino-6-methyl-1-methylenecarboxy-2-pyridinone (1.00 g, 2.98 mmol) and 2-t-butoxycarbonylamino-6-methyl-5-methylaminopyridine (0.71 g, 2.98 mmol) in methylene chloride (6 ml). After 3 h the reaction was filtered through celite and evaporated in vacuo to a pale yellow foam. Ethyl acetate (40 ml) was added resulting in a thick precipitate. HCl gas was blown onto the stirred mixture at 0° C. causing the bulk of the material to dissolve. Undissolved material was broken up with a spatula and after bubbling HCl through the mixture for 15 min dissolution was complete. Over one hour some precipitate formed. The mixture was degassed with nitrogen and was evaporated in vacuo to a solid. Water (100 ml) was added and the undissolved material was removed by filtering through a frit. The solution was washed with methylene chloride (2 times, adding sufficient brine to dissipate the emulsion) and ethyl acetate, then was basified with sodium hydrogen carbonate. The thick precipitate was collected by filtration, washing with water, methanol and ether and was dried at 50° C., 0.5 mm Hg for 64 h to give the title compound (0.83 g, 61 %) as a powder: $^1$H NMR (DMSO) δ2.23 (s, 3 H), 2.24 (s, 3 H), 4.13 (d, J=5.3 Hz, 2 H), 4.50 (s, 2 H), 4.72 (s, 2 H), 5.73 (s, 2 H), 6.08 (d, J=8.7 Hz, 1 H), 6.22 (d, J=8.2 Hz, 1 H), 7.11 (d,J=7.5 Hz, 1 H), 7.22 (d,J=8.2Hz, 1 H), 7.31–7.35 (m, 5 H), 8.47 (t, J=5.3 Hz, 1 H), 8.58 (s, 1 H); MS (FAB) 456 (M+1)$^+$

Step A': 2-Amino-5-cyano-6-methylpyridine

A mixture of 6-amino-3-bromo-2-methylpyridine (20.0 g, 0.107 mol) and copper (I) cyanide 11.0 g, 0.123 mol) in DMF (25 ml) was heated to reflux for 4 h. The DMF was evaporated in vacuo and the residue was partitioned between ethyl acetate and 10% sodium cyanide solution. The organic layer was washed with 10% sodium cyanide solution and brine, dried ($Na_2SO_4$) and evaporated in vacuo to a brown solid. This was dissolved in a minimum amount of ethyl acetate and the product was precipitated by adding hexanes. The mixture was filtered to give the title compound (12.0 g, 85%) as a brown powder: $^1$H NMR (CDC13) δ2.56 (s, 3 H), 4.97 (br s, 2 H), 6.33 (d, J=8.6 Hz, 1 H), 7.54 (d, J=8.6 Hz, 1 H).

Step B': 2-t-Butoxycarbonylamino-5-cyano-6-methylpyridine

A mixture of 2-amino-5-cyano-6-methylpyridine (10.0 g, 75.1 mmol), $(BOC)_2O$ (16.39 g, 75.1 mmol), triethylamine (11.5 ml, 82.6 mmol) and DMAP (92 mg, 7.5 mmol) in methylene chloride (200 ml) was stirred for 3 h. More triethylamine (4.22 ml) and $(BOC_2)O$ (1.64 g) were added and after 16 h the reaction was diluted with ethyl acetate and was washed with 1 M AcOH (3 times), dried ($Na_2SO_4$) and evaporated in vacuo to give dark brown solid. The crude product was purified by flash column chromatography (10% ethylacetate/hexanes) to give the title compound (14.68 g, 84%) as a white solid: $^1$H NMR ($CDCl_3$) δ1.52 (s, 9 H), 2.62 (s, 3 H), 7.46 (br s, 1 H), 7.80 (d, J=8.8 Hz, 1 H), 7.88 (d, J=8.8 Hz, 1 H).

Step C': 2-t-Butoxycarbonylamino-5-methvlamino-6-methylpyridine

A mixture of 2-t-butoxycarbonylamino-5-cyano-6-methylpyridine (14.68 g, 62.9 mmol) and 10% Pd/C (1.5 g) in glacial acetic acid (150 ml) was shaken on a Parr apparatus at 60 psi for 88 h. The reaction was filtered through celite and was evaporated in vacuo. The residue was dissolved in water and the solution was washed with methylene chloride (2 times), then was basified with sodium carbonate and extracted with ethyl acetate (2 times). The combined ethyl acetate layers were dried ($Na_2SO_4$) and evaporated in vacuo to a solid. The crude product was recrystallized (ethyl acetate/hexanes) to give the title compound (6.7 g, 45%): $^1$H NMR ($CDCl_3$) δ1.50 (s, 9 H), 2.43 (s, 3 H), 3.81 (s, 2 H), 7.23 (br s, 1 H), 7.57 (d, J=8.3 Hz, 1 H), 7.70 (d, J=8.3 Hz, 1 H).

EXAMPLE VI

Preparation of 3-Benzylsulfonylamino-1-(2-amino-6-methyl-5-methylenecarboxamidomethylpyridinyl)-2-pyridinone

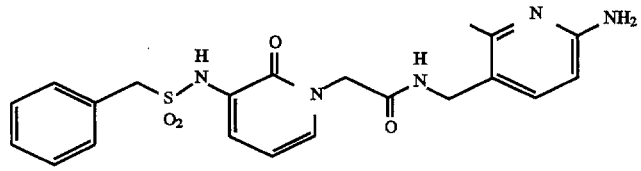

Step A: 3-Nitro-1-(t-butylmethylenecarboxy)-2-pyridinone t-Butylbromoacetate (1.48 ml, 10 mmol) was added to a stirred suspension of 2-hydroxy-3-nitropyridine (1.40 g, 10 mmol) and cesium carbonate (3.26 g, 10 mmol) in dry DMF (20 ml). After 16 h, the solvent was evaporated in vacuo and the residue was partitioned between water and ethyl acetate. The organic layer was washed with water and brine, dried ($Na_2SO_4$) and evaporated in vacuo to a ruby red solid (2.37 g): $^1H$ NMR ($CDCl_3$) δ1.49 (s, 9H), 4.68 (s, 2H), 6.34 (dd, J=6.7 and 7.6Hz, 1H), 7.60 (dd, J=2.1 and 6.7Hz, 1H), 8.38 (dd, J=2.1 and 7.6Hz, 1H).

Step B: 3-Nitro-1-methylenecarboxy-2-pyridinone

HCl gas was bubbled through a stirred suspension of 3-nitro-1-(t-butylmethylenecarboxy)-2-pyridinone (2.37 g) in ethyl acetate (50 ml) at 0° C. until a solution had formed which was saturated with HCl. After 1 h at RT the mixture was degassed with nitrogen and filtered to give the title compound (1.56 g): $^1H$ NMR (DMSO) shows loss of the t-butyl singlet.

Step C: 3-Nitro-1-(2-t-butoxycarbonylamino-6-methyl-5-methylenecarboxamidomethylpyridinvl)-2-pyridinone EDC hydrochloride (249 mg, 1.30 mmol) was added to a stirred mixture of 3-nitro-1-methylenecarboxy-2-pyridinone (198 mg, 1.00 mmol), 2-t-butoxycarbonylamino-5-methylamino-6-methylpyridine (237 mg, 1.00 mmol), HOBT (176 mg, 1.30 mmol) and triethylamine (0.32 ml, 2.30 mmol) in dry DMF (4 ml). After 16 h the solvent was evaporated in vacuo, and the residue was partitioned between methylene chloride and water. The organic layer was dried ($Na_2SO_4$) and evaporated in vacuo to a solid. Ethyl acetate was added to the crude product and the resulting mixture was heated to reflux then was cooled and filtered to give the title compound (234 mg) as a solid: $^1H$ NMR (DMSO) selected signals at δ1.45 (s, 9H, t-Bu), 2.36 (s, 3H, Me), 4.25 (d, J=5.5Hz, 2H, $NHCH_2$), 4.75 (s, 2H, $CH_2CO$).

Step D: 3-Amino-1-(2-t-butoxycarbonylamino-6-methyl-5-methylenecarboxamidomethylpyridinyl)-2-pyridinone A mixture of 3-nitro-1-(2-t-butoxycarbonylamino-6-methyl-5-methylenecarboxamidomethylpyridinyl)-2-pyridinone (234 mg) and 10% palladium on carbon (60 mg) in ethyl acetate (20 ml) was stirred under hydrogen (balloon) for 4 h. The mixture was filtered through celite and evaporated in vacuo to give the title compound (206 mg) as a solid: $^1H$ NMR (DMSO) δ1.45 (s, 9H, t-Bu), 2.36 (s, 3H, Me), 4.22 (d, J=5.5Hz, 2H, $NHCH_2$), 4.56 (s, 2H, $CH_2CO$), 5.03 (s, 2H, $NH_2$), 6.01 (t, J=7.0Hz, 1H, pyridinone H-5), 6.45 (dd, J=1.6 and 7.1 Hz, 1H, pyridinone H-4), 6.83 (dd, J=1.6 and 6.8Hz, 1H, pyridinone H-6), 7.55 (s, 2H, pyridine H's), 8.48 (br t, 1H, $NHCH_2$), 9.54 (s, 1H, BOCNH).

Step E: 3-Benzylsulfonylamino-1-(2-t-butoxycarbonylamino-6-methyl-5-methylenecarboxamidomethylpyridinyl)-2-pyridinone 3-Amino-1-(2-t-butoxycarbonylamino-6-methyl-5-methylenecarboxamidomethylpyridinyl)-2-pyridinone (206 mg) was sulfonylated using the procedure of EXAMPLE V, Step D. The crude product was purified by flash column chromatography on silica (methanol/chloroform gradient, 24% methanol) to give a foam which crystallized from ethyl acetate to the title compound (122 mg, 69%): $^1H$ NMR ($CDCl_3$) selected signals at 6 1.49 (s, 9H, t-Bu), 2.39 (s, 3H, Me), 4.27 (s, 2H), 4.38 (d, J=5.7Hz, 2H, $NHCH_2$), 4.41 (s, 2H).

Step F: 3-Benzylsulfonylamino-1-(2-amino-6-methyl-5-methylenecarboxamidomethylpyridinyl)-2-pyridinone 3-Benzylsulfonylamino-1-(2-t-butoxycarbonylamino-6-methyl-5-methylenecarboxamidomethylpyridinyl)-2-pyridinone (122 mg) was deprotected using the procedure of Step B, to give the title compound (93 mg): $^1H$ NMR (DMSO) see disappearance of the BOC 564egroup; Anal. ($C_{21}H_{23}N_5O_{4.10}$HCl. 0.6 $H_{2t\ o}$. 0.4 EtOAc).

EXAMPLE VII

Preparation of 3-Benzylsulfonylamino-6-methyl-1-(2-amino-3-methyl-5-methylenecarboxamidomethylpyridinyl)-2-pyridinone

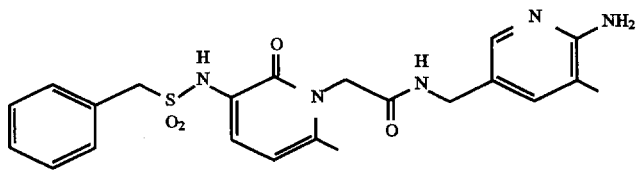

Step A: 2-Amino-5-cyano-3-methylpyridine

The title compound was prepared from 6-amino-3-bromo-5-methylpyridine using the procedure of EXAMPLE V, Step A' (the crude product was purified by trituration with hot ethyl acetate) as a tan solid: $^1H$ NMR ($CDCl_3$) δ2.15 (s, 3 H), 4.91 (br s, 2 H), 7.46 (s, 1 H), 8.25 (s, 1 H).

Step B: 2-amino-5-methylamino-3-methylpyridine

A mixture of 2-amino-5-cyano-3-methylpyridine (1.40 g) and 10% Pd/C (0.18 g) in 1:1 ethanol/1M HCl (64 ml) was shaken on a Parr apparatus at 57 psi for 16 h. The reaction was filtered through celite and was evaporated in vacuo, azeotroping with ethanol. The residue was heated to reflux as a suspension in ethanol (15 ml) then the mixture was cooled and filtered to give the title compound (0.68 g): $^1H$ NMR ($CD_3OD$) δ2.30 (s, 3 H), 4.08 (s, 2 H), 7.89 (s, 1 H), 7.91 (s, 1 H).

Step C: 3-Benzylsulfonylamino-6-methyl-1-(2-amino-3-methyl-5-methylenecarboxamidomethylpyridinyl)-2-pyridinone EDC hydrochloride (69 mg, 0.36 mmol) was added to a stirred mixture of 3-benzylsulfonylamino-6-methyl-1-methylenecarboxy-2-pyridinone (101 mg, 0.30 mmol), 2-amino-5-methylamino-3-methylpyridine (63 mg, 0.30 mmol), HOBT (49 mg, 0.36 mmol) and triethylamine (0.22 ml) in dry DMF (1.2 ml). After 64 h the reaction was evaporated in vacuo then was partitioned between ethyl acetate and water. The organic layer was washed with saturated sodium hydrogen carbonate solution and brine, dried ($Na_2SO_4$) and evaporated in vacuo to a glass. The crude product was purified by preparative HPLC ($C_{18}$, $H_2O/CH_3CN/0.1\%$ TFA gradient) to give the title compound (97 mg) as a crystalline solid, m.p. 226°–229° C.: $^1H$ NMR (DMSO) δ2.15 (s, 3 H), 2.26 (s, 3 H), 4.20 (d, J=5.5 Hz, 2 H), 4.51 (s, 2 H), 4.74 (s, 2 H), 6.11 (d, J=7.5 Hz, 1 H) 7.13 (d, J=7.5 Hz, 1 H), 7.29–7.31 (m, 5 H), 7.71–7.73 (m, 4 H),8.48 (s, 1 H), 8.76 (brt, 1 H); HFRMS (FAB) calc'd for $C_{22}H_{26}N_{5t\ o4}S$ $(M+1)^+$456.1706, found 456.1694.

EXAMPLE VIII

Preparation of 3-Benzyloxycarbonylamino-6-methyl-1-(4-methylenecarboxamidomethyl-1-amidinopiperidinyl)-2-pyridinone

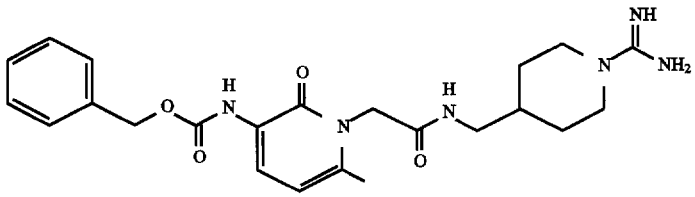

HCl gas was bubbled through a stirred suspension of 3-benzloxycarbonylamino-6-methyl-1-(4-methylenecarboxamidomethyl-1-t-butoxycarbonylpiperidinyl)-2-pyridinone (0.12 g) in ethyl acetate (5 ml) at 0° C. until a solution had formed which was saturated with HCl. After 1 h at RT a thick suspension had formed. The mixture was degassed with argon and evaporated in vacuo to give 3-benzloxycarbonylamino-6-methyl-1-(4-methylenecarboxamidomethylpiperidinyl)-2-pyridinone hydrochloride as a solid (0.10 g). Aminoiminomethanesulfonic acid (0.040 g), triethylamine (83.6 µl) and DMF (1 ml) were added to this material and the mixture was stirred at RT for 48 h. The reaction was evaporated in vacuo and the crude product was purified by preparative HPLC ($C_{18}$, 0.1 % TFA/$H_2O$,$CH_3CN$ gradient) to give the title compound as a white solid, m.p. >200° C.: $^1$H NMR ($CD_3OD$) δ1.24 (m, 2 H), 1.83 (m, 3H), 2.33 (s, 3H), 3.04 (m, 2H), 3.16 (m, 2H), 3.87 (br d, J=13.7 Hz, 2H), 4.82 (s, 2H), 5.19 (s, 2H), 6.25 (d, J =7.5 Hz, 1H), 7.28–7.32 (m, 6H), 8.34 (br m, 1H); MS (FAB) 455 (M+1)$^+$.

EXAMPLE IX

Preparation of 3-(3-Phenylpropionamido)-6-methyl-1-(4-methylene carboxamidomethyl-1-amidinopiperidinyl)-2-pyridinone

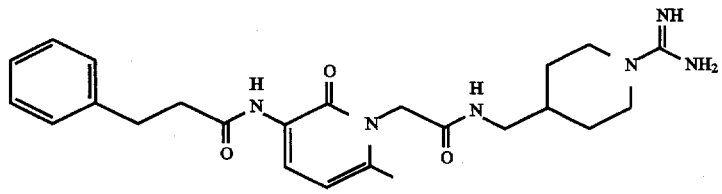

Step A: 3-(3-Phenylpropionamido)-6-methyl-1-(4-methylene-carboxamidomethyl-1-t-butoxycarbonylpiperidinyl)-2-pyridinone Hydrocinnamoyl chloride (56 mg, 0.329 mmol) was added to a stirred solution of 3-amino-6-methyl-1-(4-methylene-carboxamidomethyl-1-t-butoxycarbonylpiperidinyl)-2-pyridinone (83 mg, 0.220 nunol) and triethylamine (92 µl, 0.660 mmol) in methylene chloride (1 ml). After 16 h , the reaction directly purified by flash column chromatography on silica (eluting with 80% ethyl acetate/hexanes) to give the title compound: $^1$H NMR ($CDCl_3$) selected signals at δ1.10 (m, 2 H), 1.44 (s, 9H), 1.63 (m, 3H), 2.44 (s, 3H), 2.66 (m, 2H), 2.71 (t, J=7.8 Hz, 2H), 3.05 (t, J=7.8 Hz, 2H), 3.12 (m, 2H), 4.11 (br m, 2 H), 4.71 (s, 2H), 6.17 (d, J=7.6 Hz, 1H), 7.20–7.33 (m, 5H), 8.35 (br m, 1H).

Step B: 3-(3-Phenylpropionamido)-6-methyl-1-(4-methylene-carboxamidomethyl-1-amidinopiperidinyl)-2-pyridinone 3-(3-Phenylpropionamido)-6-methyl-1-(4-methylene-carboxamidomethyl-1-t-butoxycarbonylpiperidinyl)-2-pyridinone (0.058g) was deprotected with HCl and then amidinylated as described in EXAMPLE VIII to give the title compound as a white solid: $^1$H NMR ($CD_3OD$) δ1.24 (m, 2 H), 1.83 (m, 2H), 2.33 (s, 3H), 2.73 (t, 3H), 2.97 (t, 3H), 3.04 (m, 1H), 3.16 (m, 2H), 3.87 (br d, J=13.7 Hz, 2H), 4.80 (s, 2H), 6.25 (d, J=7.7 Hz, 1H), 7.16–7.27 (m, 6H), 8.18 (d, J=7.7 Hz, 1H), 8.30 (br m, 1H); MS (FAB) 453 (M+1)$^+$.

EXAMPLE X

Preparation of 3-(3,3-Diphenylpropionamido)-6-methyl-1-(4-methylene-carboxamidomethyl-1-amidinopiperidinyl)-2-pyridinone

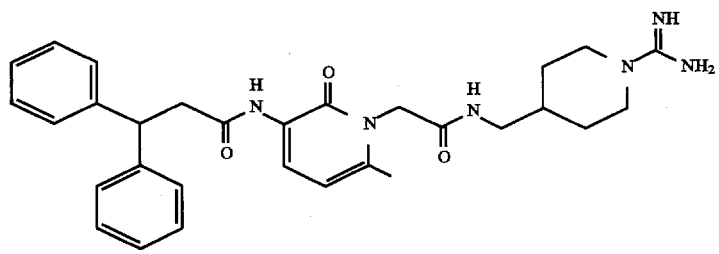

Step A: 3-(3,3-Diphenylpropionamido)-6-methyl-1-(4-methylenecarboxamidomethyl-1-t-butoxycarbonylpiperidinyl)-2-pyridinone EDC hydrochloride (75 mg, 0.393 mmol) was added to a stirred mixture of 3-amino-6-methyl-1-(4-methylenecarboxamidomethyl-1-t-butoxycarbonylpiperidinyl)-2-pyridinone (99 mg, 0.262 mmol), 3,3-diphenylpropionic acid (71 mg, 0.314 mmol), HOBT (53 mg, 0.393 mmol) and diisopropylethylamine (0.14 ml, 0.786 mmol) in dry DMF (1 ml). After 64 h the reaction was diluted with ethyl acetate and was washed with water, dried (MgSO$_4$) and evaporated in vacuo. The crude product was purified by flash column chromatography on silica (eluting with 60% ethyl acetate/hexanes) to give the title compound (62 mg): $^1$H NMR (CDCl$_3$) selected signals at δ 1.45 (s, 9H), 3.14 (d, 2H), 4.67 (br m, 3H), 7.26 (m, 10H).

Step B: 3-(3,3-Diphenylpropionamido)-6-methyl-1-(4-methylenecarboxamidomethyl-1-amidinopiperidinyl)-2-pyridinone 3-(3,3-Diphenylpropionamido)-6-methyl-1-(4-methylene-carboxamidomethyl-1-t-butoxycarbonylpiperidinyl)-2-pyridinone (0.062 g) was deprotected with HCl and then amidinylated as described in EXAMPLE VIII to give the title compound as a white solid: $^1$H NMR (CD$_3$OD) δ1.23 (m, 2 H), 1.83 (m, 2H), 2.30 (s, 3H), 3.06 (m, 1H), 3.16 (m, 2H), 3.87 (br d, J=13.7Hz, 2H), 4.60 (t, 1H), 4.78 (s, 2H), 6.18 (d, J=7.7 Hz, 1H), 7.13"7.30 (m, 6H), 8.06 (d, J=7.7 Hz, 1H), 8.29 (br m, 1H); MS (FAB) 529 (M+1)$^+$.

EXAMPLE XI

Preparation of 3-p-Toluenesulfonylamino-6-methyl-1-(4-methylene-carboxamidomethyl-1-amidinopiperidinyl)-2-pyridinone

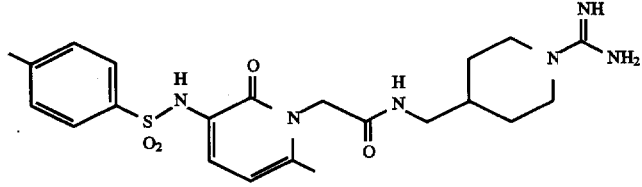

Step A: 3-p-Toluenesulfonylamino-6-methyl-1-(4-methylenecarboxamidomethyl-1-t-butoxycarbonylpiperidinyl)-2-pyridinone p-Toluenesulfonyl chloride (22 mg, 0.116 mmol) was added to a stirred solution of 3-amino-6-methyl-1-(4-methylene-carboxamidomethyl-1-t-butoxycarbonylpipelidinyl)-2-pyridinone (40 mg, 0.106 mmol) in pyridine (0.5 ml). After 2 h the reaction mixture was partitioned between 10% citric acid solution and ethyl acetate. The organic layer was dried (MgSO4), filtered and concentrated in vacuo. The resulting material was purified by flash column chromatography on silica (eluting with a methanol/chloroform gradient, 2–5% methanol) to give the title compound (27 mg). $^1$H NMR (CDCl$_3$) selected signals at δ 1.45 (s, 9H), 2.39 (s, 3H), 2.41 (s, 3H), 6.06 (d, J=7.7 Hz, 1H), 7.24 (m, 2H), 7.46 (d, J=7.7 Hz, 1H), 7.73 (m, 2H).

Step B: 3-p-Toluenesulfonylamino-6-methyl-1-(4-methylene-carboxamidomethyl-1-amidinopiperidinyl)-2-pyridinone 3-p-Toluenesulfonylamino-6-methyl-1-(4-methylenecarboxamidomeffiyl-1-t-butoxycarbonyl-piperidinyl)-2-pyridinone (0.027g) was deprotected with HCl and then amidinylated as described in EXAMPLE VIII to give the title compound as a white solid: $^1$H NMR (CD$_3$OD) δ1.23 (m, 2 H), 1.81 (m, 2H), 2.27 (s, 3H), 2.38 (s, 3H), 3.06 (m, 1H), 3.13 (m, 2H), 3.86 (br d, J=13.9 Hz, 2H), 4.67 (s, 2H), 6.15 (d, J=7.7 Hz, 1H), 7.29 (m, 2H), 7.43 (d, J=7.7 Hz, 1H), 7.71 (m, 2H), 8.23 (br m, 1H); MS (FAB) 475 (M+1)$^+$.

EXAMPLE XII

Preparation of 3-p-Toluenesulfonylamino-6-methyl-1-(methylenecarboxamido-trans-4-aminocyclohexylmethyl)-2-pyridinone

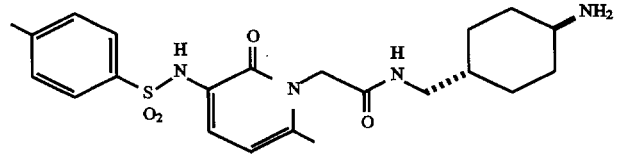

Step A: 3-p-Toluenesulfonylamino-6-methyl-1-(methylene-carboxamido-trans-4-t-butoxycarbonylaminocyclohexylmethyl)-2-pyridinone 3-Amino-6-methyl-1-(methylenecarboxamido-trans-4-t-butoxycarbonylaminocyclohexylmethyl)-2-pyridinone (20 mg, 0.051 mmol) was sulfonylated using the procedure of EXAMPLE XI, Step A to give the title compound (18 mg): $^1$H NMR (CDCl$_3$) selected signals at δ 1.44 (s, 9H), 2.39 (s, 6H), 6.07 (d, J=7.6 Hz, 1H), 7.24 (m, 2H), 7.45 (d, J=7.6 Hz, 1H), 7.73 (m, 2H).

Step B: 3-p-Toluenesulfonylamino-6-methyl-1-(methylenecarboxamido-trans-4-aminocyclohexylmethyl)-2-pyridinone 3-p-Toluenesulfonylamino-6-methyl-1-(methylenecarboxamido-trans-4-t-butoxycarbonylaminocyclohexylmethyl)-2-pyridinone (18 mg) was dissolved in ethyl acetate saturated with HCl gas (5 ml). After 45 min. the solution was degassed with argon and evaporated in vacuo to a yellow solid. The crude product was purified by preparative HPLC ($C_{18}$, 0.1% TFA/$H_2O$, $CH_3CN$ gradient) to give the title compound as a solid: $^1H$ NMR ($CD_3OD$) d 1.06 (m, 2H), 1.21 (m, 2H), 1.35 (m, 2H), 1.87 (m, 2H), 2.04 (m, 2H), 2.26 (s, 3H), 2.38 (s, 3H), 3.06 (m, 4H), 4.67 (s, 2H), 6.15 (d, J=7.1 Hz, 1H), 7.29 (m, 2H), 7.43 (d, J=7.1 Hz, 1H), 7.71 (m, 2H), 8.19 (m, 1H); MS (FAB) 447 (M+1)$^+$.

EXAMPLE XIII

Preparation of 3-Phenylacetamido-6-methyl-1-(2-amino-5-methylenecarboxamidomethylpyridinyl)-2-pyridinone

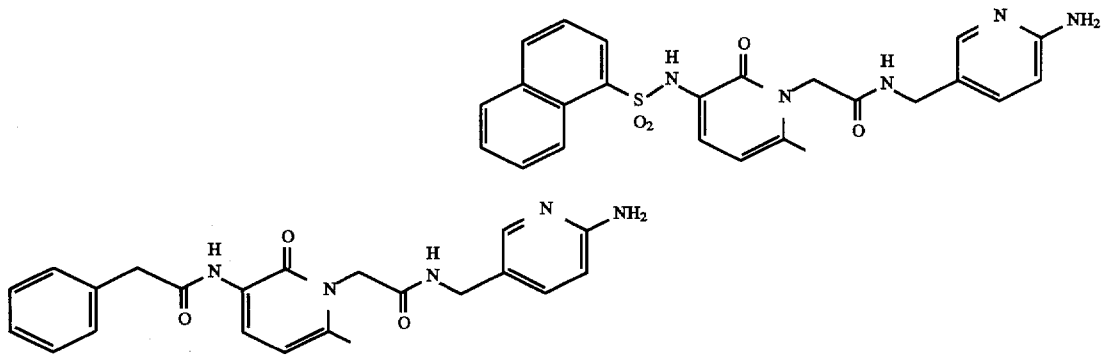

Step A: 3-Phenylacetamido-6-methyl-1-(2-t-butoxycarbonylamino-5-methylenecarboxamidomethylpyridinyl)-2-pyridinone Phenylacetyl chloride (18 mg, 0.114 mmol) was added to a stirred solution of 3-amino-6-methyl-1-(2-t-butoxycarbonylamino-5-methylenecarboxamidomethylpyridinyl)-2-pyridinone (40 mg, 0.103 mmol) in pyridine (1 ml). After 1 h the reaction mixture was partitioned between methylene chloride and water. The organic layer was washed with water and brine, dried (MgSO4), filtered and concentrated in vacuo. The resulting material was purified by flash column chromatography on silica (70% ethyl acetate/hexane) to give the title compound (28 mg): $^1H$ NMR ($CDCl_3$) selected signals at δ1.52 (s, 9H), 2.40 (s, 3H), 3.73 (s, 2H), 4.33 (m, 2H), 4.69 (s, 2H), 6.14 (d, J=7.7 Hz, 1H), 7.26–7.38 (br m, 5H).

Step B: Phenylacetamido-6-methyl-1-(2-amino-5-methylenecarboxamidomethylpyridinyl)-2-pyridinone The title compound was prepared from phenylacetamido-6-methyl-1-(2-t-butoxycarbonylamino-5-methylenecarboxamidomethylpyridinyl)- 2-pyridinone (0.028 g) using the procedure of EXAMPLE XII, Step B as a white solid (4.2 mg). $^1H$ NMR ($CD_3OD$) δ 2.31 (s, 3H), 3.75 (s, 2H), 4.29 (s, 2H), 4.73 (s, 2H), 6.23 (d, J=7.5 Hz, 1H), 6.97 (d, J=8.9 Hz, 1H), 7.27–7.34 (m, 6H), 7.76–7.86 (m, 2H), 8.18 (m, 1H); MS (FAB) 406 (M+1)$^+$.

EXAMPLE XIV

Preparation of 3-(1-Napthylsulfonyl)amino-6-methyl-1-(2-amino-5-methylenecarboxamidomethylpyridinyl)-2-pyridinone The title compound was prepared from 1-napthylsulfonyl chloride (64 mg, 0.283 mmol) and 3-amino-6-methyl-1-(2-t-butoxycarbonylamino-5-methylenecarboxamidomethylpyridinyl)-2-pyridinone (0.100 g, 0.258 mmol) using the procedure of EXAMPLE XIII, as a white solid, m.p.>200° C.: $^1H$ NMR ($CD_3OD$) δ2.22 (s, 3H), 4.24 (s, 2H), 4.62 (s, 2H), 6.10 (d, J=7.6 Hz, 1H), 6.96 (d, J=9.3 Hz, 1H), 7.32 (d, J=9.3 Hz, 1H), 7.51–7.61 (m, 3H), 7.73 (s, 1H), 7.84 (dd, J=2.2 and 9.2 Hz, 1H), 7.96 (m, 1H), 8.12 (d, J=8.3 Hz, 1H), 8.24 (m, 1H), 8.68 (m, 2H); MS (FAB) 478 (M+1)$^+$.

EXAMPLE XV

Preparation of 3-(2-Napthylsulfonyl)amino-6-methyl-1-(2-amino-5-methylenecarboxamidomethylpyridinyl)-2-pyridinone

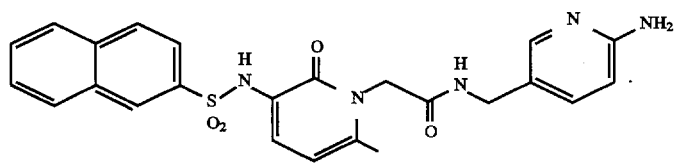

The title compound was prepared from 3-amino-6-methyl-1-(2-t-butoxycarbonylamino-5-methylenecarboxamidomethylpyridinyl)-2-pyridinone (0.100 g, 0.258 mmol) and 2-naphthylsulfonyl chloride (64 mg, 0.283 mmol) using the procedure of EXAMPLE XIII as a white solid, m.p. 188°–190° C.: $^1$H NMR (CD$_3$OD) δ2.25 (s, 3H), 4.21 (s, 2H), 4.65 (s, 2H), 6.17 (d, J=7.6 Hz, 1H), 6.91 (d, J=9.0 Hz, 1H), 7.10–7.23 (m, 4H), 7.52–7.99 (m, 9H), 8.41 (m, 1H); MS (FAB) 478 (M+1)$^+$.

EXAMPLE XVI

Preparation of 3-(4-Trifluoromethylbenzylsulfonyl)amino-6-methyl-1-(2-amino-6-methyl-5-methylenecarboxamidomethylpyridinyl)-2-pyridinone

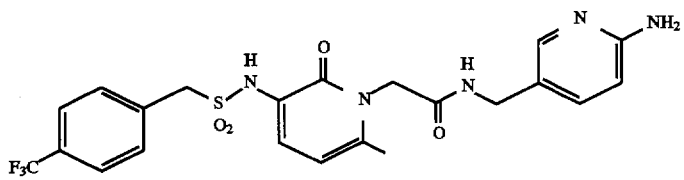

Step A: 4-Trifluoromethylbenzylsulfonyl chloride

A mixture of 4-trifluoromethylbenzyl chloride (1.0 g, 5.14 mmol) and sodium thiosulfate (0.813 g, 5.14 mmol) in methanol (1.5 ml) and H$_2$O (1.5 ml) was heated to reflux for 3 h. The mixture was cooled to 0° C. and glacial acetic acid (1.5 ml) and ice were added. Chlorine gas was bubbled through the resulting suspension for 1 h, periodically adding ice to maintain an ice/liquid mixture. After an additional hour, the reaction was extracted with ether and the ether layer was washed with 5% sodium bisulfite and water, dried (MgSO$_4$), filtered, and evaporated in vacuo to give the title compound as a white solid (0.932 g).

Step B: 3-(4-Trifluoromethylbenzylsulfonyl)amino-6-methyl-1-(2-t-butoxycarbonylamino-6-methyl-5-methylenecarboxamidomethylpyridinyl)-2-pyridinone The title compound was prepared from 3-amino-6-methyl-1-(2-t-butoxycarbonylamino-6-methyl-5-methylenecarboxamido-methylpyridinyl)-2-pyridinone (0.100 g, 0.249 mmol) and 4-trifluoromethylbenzylsulfonyl chloride (64 mg, 0.249 mmol) using the procedure of EXAMPLE XIII, as a white solid (60 mg), m.p. >200° C.: $^1$H NMR (CD$_3$OD) δ2.30 (s, 3 H), 2.51 (s, 3 H), 4.32 (d, J=5.6 Hz, 2 H), 4.55 (s, 2 H), 4.79 (s, 2 H), 6.10 (d, J=7.6 Hz, 1 H), 6.81 (d, J=9.3 Hz, 1 H), 7.31 (d, J=7.8 Hz, 1 H), 7.51 (d, J=8.3 Hz, benzene aromatic H$_A$), 7.58 (d, J=8.3 Hz, benzene aromatic HB), 7.88 (d, J=9.0 Hz, 1H), 8.75 (m, 1H); MS (FAB) 524 (M+1)$^+$.

EXAMPLE XVII

Preparation of 3-(2-Napthylsulfonyl)amino-6-methyl-1-(2-amino-6-methyl-5-methylenecarboxamidomethylpyridinyl)-2-pyridinone

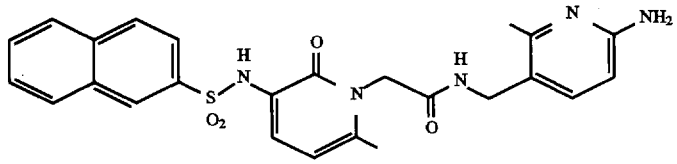

The title compound was prepared from 3-amino-6-methyl-1-(2-t-butoxycarbonylamino-6-methyl-5-methylenecarboxamido-methylpyridinyl)-2-pyridinone (0.100 g, 0.249 mmol) and 2-napthylsulfonyl chloride (56 mg, 0.249 mmol) using the procedure of EXAMPLE XIII, as a white solid (72 mg), m.p. >200° C.: $^1$H NMR (CD$_3$OD) δ2.23 (s, 3H), 2.44 (s, 3 H), 4.20 (d, J=5.9 Hz, 2 H), 4.63 (s, 2 H), 6.16 (d, J=8.1 Hz, 1 H), 6.75 (d, J=9.3 Hz, 1 H), 7.10–7.23 (m, 2H), 7.51–8.00 (m, 7H), 8.41 (s, 1H), 8.59 (m, 1H); MS (FAB) 492 (M+1)$^+$.

EXAMPLE XVIII

Preparation of 3-(4-Fluorobenzylsulfonyl)amino-6-methyl-1-(2-amino-6-methyl-5-methylenecarboxamidomethylpyridinyl)-2-pyridinone

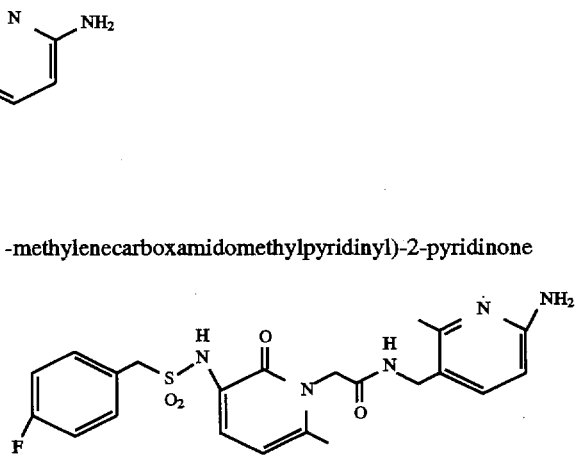

Step A: The title compound was prepared from 4-fluoromethylbenzyl chloride (1.0 g) using the procedure of EXAMPLE XVI, Step A, as a heavy oil. Step B: The title compound was prepared from 3-amino-6-methyl-1-(2-t-butoxycarbonylamino -6-methyl-5-methylenecarboxamidomethyl-pyridinyl)-2-pyridinone (0.100 g, 0.249 mmol) and 4-fluoromethylbenzylsulfonyl chloride (52 mg, 0.246 mmol) using the procedure of EXAMPLE XIII, as a white solid: $^1$H NMR (CD$_3$OD) δ2.33 (s, 3 H), 2.51 (s, 3 H), 4.32 (d, J=5.9 Hz, 2 H), 4.43 (s, 2 H), 4.80 (s, 2 H), 6.16 (d, J=7.3 Hz, 1 H), 6.80 (d, J=8.8 Hz, 1 H), 6.97 (m, 2 H), 7.01–7.34 (m, 3H), 7.88 (d, J=9.0 Hz IH), 8.75 (m, 1H); MS (FAB) 474 (M+1)$^+$.

EXAMPLE XIX

Preparation of 3-(2-Phenethylamino)-6-methyl-1-(2-amino-6-methyl-5-methylenecarboxamidomethylpyridinyl)-2-pyridinone

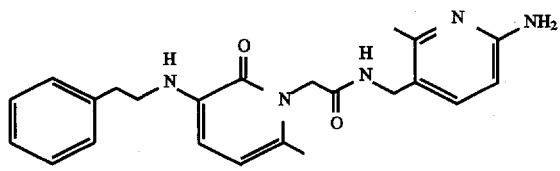

The title compound was prepared from 3-amino-6-methyl-1-(2-t-butoxycarbonylamino-6-methyl-5-methylenecarboxamidomethylpyridinyl)- 2-pyridinone (0.060 g, 0.15 mmol) and phenylacetaldehyde (19.5 μl, 0.165 mmol) using the procedure of EXAMPLE III, as a pale yellow solid, m.p. >200° C.: ¹H NMR (CD₃OD) δ2.25 (s, 3H), 2.50 (s, 3 H), 2.92 (m, 2H), 3.30 (m, 2H), 4.28 (d, J=5.6 Hz, 2 H), 4.76 (s, 2 H), 6.16 (d, J=7.3 Hz, 1 H), 6.41 (d, J=7.3 Hz, 1 H), 6.81 (d, J=9.3 Hz, 1H), 7.18–7.28 (m, 4H), 7.85 (d, J=9.3 Hz, 1H), 8.65 (m, 1H); MS (FAB) 406 (M+1)⁺.

EXAMPLE XX

Preparation of 3-Benzylsulfonylamino-6-methyl-1-(2-amino-4-methyl-5-methylenecarboxamidomethylpyridinyl)-2-pyridinone

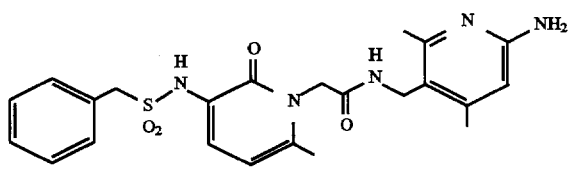

The title compound was prepared from 2-amino-5-bromo-4-methylpyridine using the procedure of EXAMPLE VII, as a solid, m.p. >200° C.: ¹H NMR (CD30D) selected signals at δ2.35 (s, 3H), 2.41 (s, 3H), 4.34 (s, 2H), 4.44 (s, 2H), 4.81 (s, 2H), 6.18 (d, J=7.5 Hz, 1H), 6.81 (s, 1H), 7.24–7.30 (m, 5H), 7.32 (d, J=7.7 Hz, 1H), 7.76 (s, 1H); HRMS (FAB) calc'd for C₂₂H₂₆N₅O₄S (M+1)⁺456.1705, found 456.1706.

EXAMPLE XXI

Preparation of 3-Benzylsulfonylamino-6-methyl-1-(2-amino-4,6-dimethyl-5-methylenecarboxamidomethylpyridinyl)-2-pyridinone

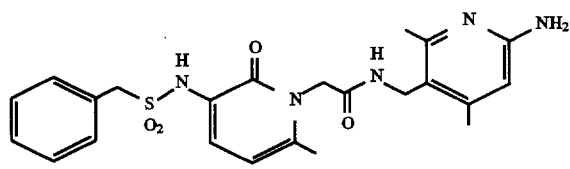

The title compound was prepared from 3-benzylsulfonylamino-6-methyl-1-methylenecarboxy-2-pyridinone (100 mg, 0.297 mmol) and 2-t-butoxycarbonylamino-4,6-dimethyl-5-methylaminopyridine [which was prepared from 2-amino-5-cyano-4,6-dimethylpyridine using the procedure of EXAMPLE V, Steps B' and C' (75 mg, 0.297 mmol)] using the procedure of EXAMPLE V, Step F, as a solid: ¹H NMR (DMSO) selected signals at δ2.22 (s, 3 H), 2.35 (s, 3 H), 4.21 (d, 2 H), 4.50 (s, 2 H), 4.67 (s, 2 H), 6.09 (d, 1 H), 6.63 (s, 1H), 7.09 (d, 1 H), 7.11–7.32 (m, 5 H), 7.54 (br s, NH), 8.53 (br s, NH); HRMS (FAB) calc'd for C₂₃H₂₈N₅O₄S (M+1) ⁺470.1862, found 470.1859.

EXAMPLE XXII

Preparation of 3-(4-Chlorobenzylsulfonylamino)-6-methyl-1-(2-amino-6-methyl-5-methylenecarboxamidomethylpyridinyl)-2-pyridinone

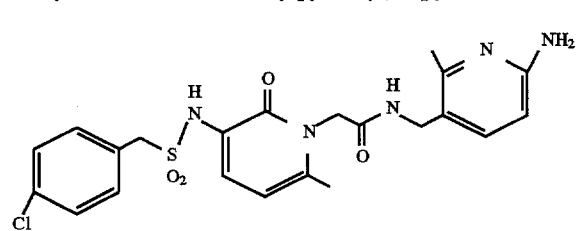

Step A: 3-(4-Chloro-benzylsulfonylamino)-6-methyl-1-(t-butyl-methylenecarboxy)-2-pyridinone The title compound was prepared from 4-chlorobenzylsulfonyl chloride (336 mg, 1.49 mmol) and 3-amino-6-methyl-1-(2-t-butoxycarbonylamino-6-methyl-5-methylenecarboxamidomethylpyridinyl)-2-pyridinone (400 mg, 0.996 mmol) using the procedure of EXAMPLE XII, Step A, as a pale pink solid (from ethyl acetate): ¹H NMR (CDCl₃) selected signals at δ1.50 (s, 9 H, t-Bu), 2.40 (s, 3 H), 2.46 (s, 3H), 4.16 (s, 2H), 4.37 (d, J=5.7 Hz, 2H), 4.45 (s, 2H), 6.09 (d, J=7.9 Hz, 1 H, pyridinone H-5), 7.07–7.15 (m, 4 H), 7.11 (d, J=7.5 Hz, 1H, pyridinone H-4), 7.51 (d, J=8.2 Hz, 1H), 7.64 (d, J=8.2 Hz, 1H), 8.22 (br s, 1H).

Step B: 3-(4-Chloro-benzylsulfonylamino)-6-methyl-1-(2-amino-6-methyl-5-methylenecarboxamidomethylpyridinyl)-2-pyridinone HCl gas was bubbled through a stirred suspension of 3-(4-chloro-benzylsulfonylamino)-6-methyl-1-(t-butyl-methylenecarboxy)-2-pyridinone (325 mg, 14.52 mmol) in ethyl acetate (10 ml) at 0° C. until a solution had formed which was saturated with HCl. After 1.5 h a thick suspension had formed. The mixture was degassed with argon and filtered to give the title compound (202 mg) as a solid, m.p.>200° C.: ¹H NMR (DMSO) see disappearance of the BOC group; HRMS (FAB) calc'd for C₂₂H₂₅N₅O₄SCl (M+1)⁺490.1316, found 490.1300.

EXAMPLE XXIII

Preparation of 3-Benzylsulfonylamino-6-trifluoromethyl-1-(2-amino-6-methyl-5-methylenecarboxamidomethylpyridinyl)-2-pyridinone

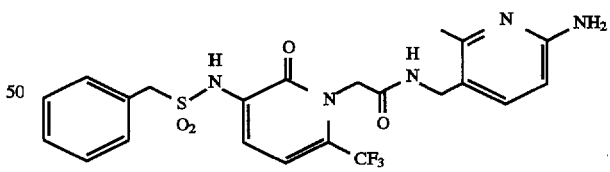

Step A: 3 -Nitro-6-trifluoromethyl-2-pyridinone

Butyl-2-trifluoroacetylvinylether (13.79 g, 70.29 mmol) and nitroacetamide (6.65 g, 63.90 mmol) were added to a stirred solution of sodium ethoxide (4.35 g, 63.90 mmol) in ethanol (320 ml). After heating the reaction at reflux for 24 h the residue was taken up in ethyl acetate and washed with 1M HCl (two times), dried (Na₂SO₄), and evaporated in vacuo. The crude product was purified by flash column chromatography on silica (eluting with 20% ethyl acetate/2% acetic acid/hexane) to give the title compound (5.73 g): ¹H NMR (CD₃OD) selected signals at δ7.35 (d, J=8.1 Hz, 1H), 8.49 (d, J=8.1 Hz, 1H).

Step B: 3-Nitro-6-trifluoromethyl-1-allyl-2-pyridinone

A solution of allyl acetate (13.5 ml, 125 mmol) in THF (8 ml), was evacuated and purged with argon (3 times). Palladium acetate (122 mg, 0.50 mmol) and triphenylphosphine (525 mg, 2.0 mmol) were added as solutions in tetrahydrofuran (1.5 ml each), followed by 3-nitro-6-trifluoromethyl-2-pyridinone (2.6 g, 12.5 mmol) in THF (2 ml). The reaction was heated to reflux for 64 h, and more allyl acetate (13.5 ml, 125 mmol), triphenylphosphine (525 mg, 2.0 mmol), palladium acetate (122 mg, 0.5 mmol), and tetrahydrofuran (13 ml) were added. After a further 24 h and 48 h at reflux addditional allyl acetate (13.5 ml, 125 mmol), palladium acetate (122 mg, 0.5 mmol), and triphenylphosphine (525 mg, 2.0 mmol) were added and the reaction was heated to reflux for a further 24 h. The reaction was cooled and evaported in vacuo to a gum which was purified by flash column chromatography on silica (15% ethyl acetate/hexane) to give the product contaminated with unreacted 3-nitro-6-trifluoromethyl-2-pyridinone. This material was diluted with ethyl acetate and washed with water adjusted to pH 12 with sodium carbonate, dried ($Na_2SO_4$), and evaporated in vacuo to give the title compound (1.05 g): $^1$H NMR ($CDCl_3$) selected signals at δ4.80 (d, J=5.8 Hz, 2H), 5.28–5.33 (m, 2H), 5.86–5.96 (m, 1H), 6.80 (d, J=7.9 Hz, 1H), 8.22 (d, J=7.9 Hz, 1H).

Step C: 3-Amino-6-trifluoromethyl-1-allyl-2-pyridinone

A solution of tin(II) chloride (924 mg, 4.09 mmol) in concentrated HCl (2.5 ml) was added dropwise to a stirred solution of 3-nitro-6-trifluoromethyl-1-allyl-2-pyridinone (127 mg, 0.512 mmol) in THF (6.5 ml) at −10° C. After 1 h at 0° C., the reaction was poured into a mixture of 50% sodium hydroxide and ice. The product was extracted into ethyl acetate, dried ($Na_2SO_4$), and evaporated in vacuo to give the title compound (106 mg): $^1$H NMR ($CDCl_3$) selected signals at δ 4.63 (br s, 2H, $NH_2$), 4.74 (d, J=5.4 Hz, 2H), 5.11–5.23 (m, 2H), 5.86–5.99 (m, 1H), 6.42 (d, J=7.7 Hz, 1H), 6.64 (d, J=7.7 Hz, 1H).

Step D: 3-Benzylsulfonylamino-6-trifluoromethyl-1-allyl-2-pyridinone

Benzylsulfonyl chloride (103 mg, 0.542 mmol) was added to a stirred solution of 3-amino-6-trifluoromethyl-1-allyl-2-pyridinone (106.5 mg, 0.488 mmol) in pyridine (1 ml) at 0° C. After 1 h the reaction was evaporated in vacuo and the residue was partitioned between methylene chloride and 10% potassium hydrogen sulfate solution, dried ($Na_2SO_4$), and evaporated in vacuo to give the title compound (175.8 mg): $^1$H NMR ($CDCl_3$) selected signals at δ4.42 (s, 2H), 4.74 (d, J=5.5 Hz, 2H), 5.16–5.31 (m, 2H), 5.86–5.96 (m, 1H), 6.55 (d, J=7.7 Hz, 1H), 7.11 (d, J=7.9 Hz, 1H), 7.27–7.33 (m, 5H), 7.70 (br s, 1H, NH).

Step E: 3-Benzylsulfonylamino-6-trifluoromethyl-2-pyridinone-1-methylenecarboxaldehyde Sodium periodate (414 mg, 1.935 mmol) and ruthenium (III) chloride hydrate (2.15 mg, 0.0104 mmol) were added a mixture of 3-benylsulfonylamino-6-trifluoromethyl-1-allyl-2-pyridinone (176 mg, 0.472 mmol) in carbon tetrachloride (0.94 ml), water (1.41 ml), and acetonitrile (0.94 ml). After 3 h, the reaction was diluted with methylene chloride, washed with water, dried ($Na_2SO_4$), and evaporated in vacuo to give the title compound (137.5 mg): $^1$H NMR (DMSO) selected signals at δ4.65 (s, 2H), 4.99 (s, 2H), 6.80 (d, J=8.1 Hz, 1H), 7.16 (d, J=7.8 Hz, 1H), 7.28–7.35 (m, 5H), 9.36 (s, 1H, NH), 9.63 (s, 1H, CHO).

Step F: 3-Benzylsulfonylamino-6-trifluoromethyl-1-methylenecarboxy-2-pyridinone

Jones Reagent (2.7M) was added dropwise to a stirred solution of 3-benzylsulfonylamino-6-trifluoromethyl-2-pyridinone-1-methylenecarboxaldehyde (89 mg) in acetone (5 ml) at 0° C. until the color remained orange. Ethanol was added until the reaction changed to a green color and the mixture was diluted with ethyl acetate and washed with water, dried ($Na_2SO_4$), and evaporated in vacuo to give the title compound (84 mg): $^1$H NMR (DMSO) shows the disappearance of the aldehyde peak.

Step G: 3-Benzylsulfonylamino-6-trifluoromethyl-1-(2-amino-6-methyl-5-methylenecarboxamidomethylpyridinyl)-2-pyridinone DCC (31 mg, 0.151 mmol) was added to a stirred solution of 3-benzylsulfonylamino-6-trifluoromethyl-1-methylenecarboxy-2-pyridinone (59 mg, 0.151 mmol) and 2-t-butoxycarbonylamino-6-methyl-5-aminomethylpyridine (39 mg, 0.166 mmol) in methylene chloride (0.55 ml). After 3 h the reaction was filtered through a cotton wool plug and evaporated in vacuo. The residue was taken up in methanol, filtered and purified by preparative HPLC ($C_{18}$, 0.1 % TFA,$H_2O$/$CH_3CN$ gradient) followed by flash column chromatography on silica (3:1 hexane/acetone then 50% ethyl acetate/1% acetic acid/hexane) to give the coupled product (53 mg). Ethyl acetate (5 ml) was added and HCl gas was bubbled through the stirred mixture at 0° C. until the reaction was a saturated solution. After 3 h at RT, the reaction was degassed with argon and filtered to give the title compound (38 mg), m.p. 161°–168° C.: $^1$H NMR (DMSO) selected signals at δ2.42 (s, 3H), 4.17 (d, J=5.5 Hz, 2H), 4.66 (d, J=6.6 Hz, 2H), 6.79 (d, J=7.9Hz, 2H), 7.16 (d, J=8.1 Hz, 1H), 7.29–7.33 (m, 5H), 7.61 (br s, 2H, $NH_2$), 7.74 (d, J=9.0 Hz, 1H), 8.71 (t, 1H, NH), 9.26 (s, 1H, NH); HRMS (FAB) calc'd for $C_{22}H_{23}N_5O_4F_3S$ $(M+1)^+$ 510.1423, found 510.1421.

EXAMPLE XXIV

Preparation of 3-(4-Chlorobenzylsulfonylamino)-6-trifluoromethyl-1-(2-amino-6-methyl-5-methylenecarboxamidomethylpyridinyl)-2-pyridinone

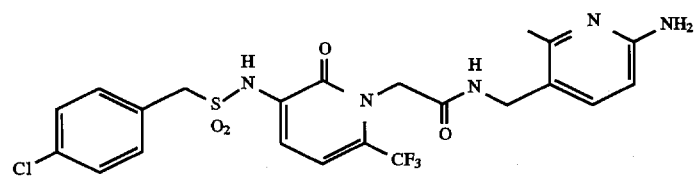

The title compound was prepared 4-chlorobenzylsulfonyl chloride using the procedures of EXAMPLE XXIII, Steps D–G, as a white solid, m.p. 170°–198° C.: $^1$H NMR (CD$_3$OD) selected signals at δ 2.51 (s, 3H), 4.32 (s, 2H), 4.54 (s, 2H), 4.80 (s, 2H), 6.75 (d, J=8.1 Hz, 1H), 6.81 (d, J=9.0 Hz, 1H), 7.24–7.44 (m, 5H), 7.86 (d, J=9.0 Hz, 1H), 8.70 (t, 1H, NH); HRMS (FAB) calc'd for C$_{22}$H$_{22}$N$_5$O$_4$SClF$_3$ (M+1)$^+$544.1033, found 544.1029.

EXAMPLE XXV

Preparation of 3-Benzylsulfonylamino-6-methyl-1-[4-methylenecarboxamidomethyl-1-(hydroxyamino) iminomethylpiperidinyl]-2-pyridinone sodium carbonate (0.108 g, 1.02 mmol). The resulting suspension was stirred at RT for 15 min and the insoluble material removed by filtration. The filtrate was then combined with 3-benzylsulfonylamino-6-methyl-1-(4-methylenecarboxamidomethyl-1-cyanopiperidinyl)-2-pyridinone (86.8 mg, 0.190 umnol), stirred at RT for 3 h, concentrated in vacuo, and purified by preparative HPLC (C$_{18}$, 0.1 % TFA/H$_2$O, CH$_3$CN gradient) to give the title compound (55 mg) as a white solid, m.p. 79°–81° C.: $^1$H NMR (CD$_3$OD) δ1.25 (m, 2 H), 1.84 (m, 3H), 2.33 (s, 3H), 3.04 (m, 2H), 3.16 (m, 2H), 3.78 (br d, J=13.4 Hz, 2H), 4.45 (s, 2H), 4.79 (s, 2 H), 6.15 (d, J=7.8 Hz, 1H), 7.13–7.31 (m, 6H), 8.34 (br m, 1H); MS (FAB) 491 (M+1)$^+$.

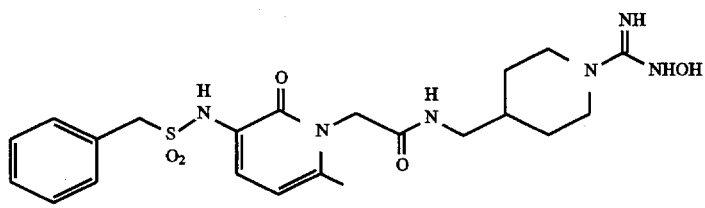

Step A: 3-Benzylsulfonylamino-6-methyl-1-(4-methylenecarboxamidomethylpiperidinyl)-2-pyridinone The title compound was prepared from 3-benzylsulfonyl-amino-6-methyl-1-methylenecarboxy-2-pyridinone (0.500 g, 1.49 mmol) and 4-aminomethyl-1-t-butoxycarbonylpiperidine (0.318 g, 1.49 mmol) using the procedure of EXAMPLE V, Step F, as a foam (0.764 g): $^1$H NMR (CD$_3$OD) δ 1.40 (m, 2 H), 1.80 (m, 3H), 2.33 (s, 3H), 2.97 (m, 2H), 3.22 (m, 2H), 3.42 (br d, J=15.1 Hz, 2H), 4.45 (s, 2H), 4.79 (s, 2 H), 6.15 (d, J=7.6Hz, 1H), 7.29–7.34 (m, 6H), 8.37 (brm, 1H).

Step B: 3-Benzylsulfonylamino-6-methyl-1-(4-methylenecarboxamidomethyl-1-cyanopiperidinyl)-2-pyridinone To a stirred solution of 3-benzylsulfonylamino-6-methyl-1-(4-methylenecarboxamidomethylpiperidinyl)-2-pyridinone (0.100 g, 0.231 mmol) and sodium acetate (94.7 mg, 1.16 mmol) in methanol (2 ml) was added cyanogen bromide (48.9 mg, 0.462 mmol). The resulting heterogeneous mixture was stirred at RT for 3.5 h and concentrated in vacuo. The crude product was purified by flash column chromatography on silica (methanol/chloroform gradient, 2–10% methanol) to give the title compound (87 mg): $^1$H NMR (CD$_3$OD) shows a downfield shift of the piperidine H's compared to the starting material.

Step C: 3-Benzylsulfonylamino-6-methyl-1-[4-methylenecarboxamidomethyl-1-(hydroxyamino) iminomethylpiperidinyl]-2-pyridinone To a stirred solution of hydroxylamine hydrochloride (0.143 g, 2.07 mmol) in methanol (2.5 ml) was added solid

EXAMPLE XXVI

Preparation of (+/−)-3-(α-Methylbenzylsulfonylamino)-6-methyl-1-(2-amino-6-methyl-5-methylenecarboxamidomethylpyridinyl)-2-pyridinone

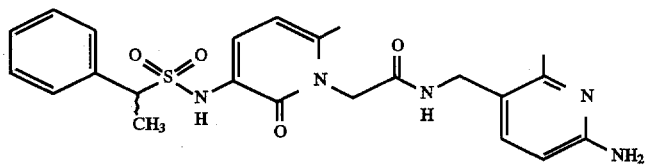

Step A: (+/−)-3-(α-Methylbenzylsulfonylamino)-6-methyl-1-(t-butyl-methylenecarboxy)-2-pyridinone A solution of lithium diisopropylamide in THF (0.393 M, 14.2 ml, 5.60 mmol, 2.2 equiv) was added to a solution of 3-benzylsulfonylamino-6-methyl-1-(t-butyl-methylenecarboxy)-2-pyridinone (1.00 g, 2.55 mmol) in THF (20 mL) at −78° C. under argon. The resulting yellow suspension was warmed to 0° C. and held at that temperature for 5 min, then cooled to −78° C. and stirred for 15 min. Iodomethane (0.800 mL, 12.8 mmol, 5.4 equiv) was added, and the reaction mixture was warmed to 0° C. and stirred for 1 h. The product solution was partitioned between aqueous half-saturated ammonium chloride solution (150 mL) and ethyl acetate (150 mL). The aqueous phase was separated and extracted further with ethyl acetate (150 mL). The combined organic layers were dried over sodium sulfate and concentrated. The residue was purified by flash column chromatography (20% ethyl acetate in hexane initially, grading to 40% ethyl acetate in hexane) to afford a 10:1 mixture of (+/−)-3-benzylsulfonylamino-6-methyl-1-α-(t-butoxycarbonylethyl)-2-pyridinone and (+/−)-3-(α-methylbenzylsulfonylamino)-6-methyl-1-(t-butyl-methylenecarboxy)-2-pyridinone, respectively, as a colorless oil (410 mg, 40%). In the major product: $^1$H NMR (CDCl₃) δ4.82 (br, 1H, NCHCH₃CO) replaces δ 4.89 (s, 2H, NCH₂CO) in the spectrum of the starting material.

Step B: (+/−)-3-(α-Methylbenzylsulfonylamino)-6-methyl-1-(2-amino-6-methyl-5-methylenecarboxamidomethylpyridinyl)-2-pyridinone The mixture of t-butyl esters (410 mg, 1.01 mmol) was deprotected using the procedure of EXAMPLE IV, Step E. The mixture of resulting carboxylic acids was then coupled to 2-t-butoxycarbonyl-amino- 5-methylamino-6-methylpyridine (233 mg, 0.982 mmol) using the procedure of EXAMPLE IV, Step F. The major, undesired amide product was separated from the minor, desired component by fractional recrystallization from 60:40:5 hexane/ethyl acetate/methanol: ¹H NMR (CDCl₃) selected peaks at δ5.10 (br, 1H, CHCH₃), 4.30 (s, 2H, BnCH₂), 1.73 (d, 3H, J=7.0 Hz, CHCH₃). The mother liquor was purified by preparative TLC (60:40:5 hexane/ethyl acetate/methanol) to give the desired amide product: ¹H NMR (CDCl₃) selected peaks at δ4.26 (q, 1H, J=7.1 Hz, CHCH₃), 4.51 (s, 2H, NCH₂), 1.70 (d, 3H, J=7.1 Hz, CHCH₃). Treatment of the desired product with a solution of TFA/CH₂Cl₂ (1:1) for 2.5 h at 23° C. followed by concentration afforded the title compound as a white solid (7 mg, mp 105°–120° C., deformed): ¹H NMR shows loss of BOC group; HRMS (FAB) Calc'd for C₂₃H₂₈N₅O₄S [M+H]⁺: 470.1852; Found: 470.1862.

EXAMPLE XXVII

Preparation of: 3-(3-Chlorobenzyl)sulfonylamino-6-methyl-1-(2-amino-6methyl-5-methylenecarboxamidomethylpyridinyl)-2-pyridinone

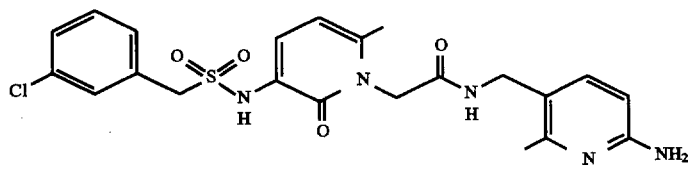

The title compound was prepared from 3-amino-6-methyl-1-(2-t-butoxycarbonylamino-6-methyl-5-methylenecarboxamidomethyl-pyridinyl)-2-pyridinone (75 mg, 0.187 mmol) and 3-chlorobenzylsulfonyl chloride (84 mg, 0.356 mmol) using the procedure of EXAMPLE XIII, as an amorphous solid (TFA salt): ¹H NMR (DMSO) δ2.25 (s, 3 H), 2.41 (s, 3 H), 4.17 (d, J=5.5Hz, 2 H), 4.56 (s, 2 H), 4.73 (s, 2 H), 6.10 (d, J=7.5 Hz, 1 H), 6.76 (br s, 1 H), 7.16 (d, J=7.5 Hz, 1 H), 7.33–7.45 (m, 5 H), 7.78 (br s, 1 H), 8.73 (s, 1 H); MS (FAB) 490 (M+1)⁺.

Following the same procedure as above the following compounds were prepared:

EXAMPLE XXVIII

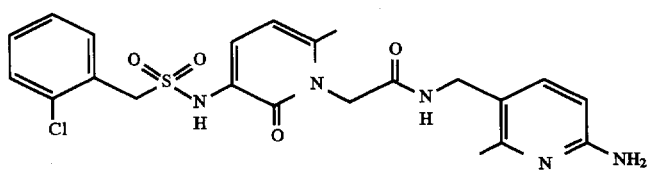

3-(2-Chlorobenzyl)sulfonylamino-6-methyl-1-(2-amino-6-methyl-5-methylenecarboxamidomethylpyridinyl)-2-pyridinone (TFA salt); ¹H NMR (DMSO) δ2.26 (s, 3 H), 2.40 (s, 3 H), 4.17 (d, J=5.7 Hz, 2 H), 4.66 (s, 2 H), 4.73 (s, 2 H), 6.12 (d, J=8.1 Hz, 1 H), 6.72 (d, J=7.7 Hz, 1 H), 7.18 (d, J=7.5 Hz, 1 H), 7.29–7.55 (m, 4 H), 7.73 (d, J=9.1 Hz, 1 H), 8.72–8.73 (m, 1 H), 8.87 (s, 1H); MS (FAB) 490 (M+1)⁺.

EXAMPLE XXIX

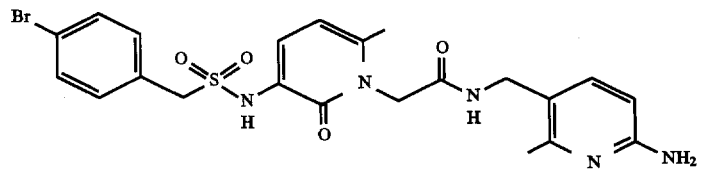

3-(4-Bromobenzyl)sulfonylamino-6-methyl-1-(2-amnino-6-methyl-5-methylenecarboxamidomethylpyridinyl)-2-pyridinone (TFA salt); ¹H NMR (DMSO) δ2.25 (s, 3 H), 2.42 (s, 3 H), 4.18 (d, J=5.7 Hz, 2 H), 4.53 (s, 2 H), 4.72 (s, 2 H), 6.09 (d, J=7.9 Hz, 1 H), 6.79 (d, J=7.5 Hz, 1 H), 7.15 (d, J=7.5 Hz, 1 H), 7.30–7.51 (m, 4 H), 7.79 (d, J=7.5 Hz, 1H), 8.63 (s, 1H), 8.70–8.78 (m, 1H); MS (FAB) 536 (M+1)⁺.

EXAMPLE XXX

Preparation of 3-Benzylsulfonylamino-6-methyl-1-(2-amino-6-ethyl-5-methylenecarboxamidomethylpyridinyl)-2-pyridinone

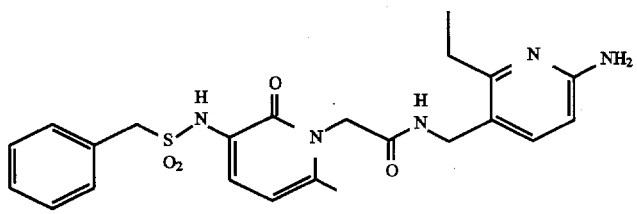

Step A: 2-t-Butoxycarbonylamino-5-cyano-6-ethylpyridine

To a stirred solution of 2-t-butoxycarbonylaliino-5-cyano-6-methylpyridine (0.50g, 2.145 mmol) in dry THF (15 ml) at -78° C. was added n-BuLi (1.75 ml, 2.5 M in hexanes) dropwise. The solution turned deep red upon addition of the second equivalent of base. After 0.5 h methyl iodide (0.67 ml, 10.7 mmol) was added. After 1 h half saturated NH₄Cl (15 ml) was added, the layers were separated and the aqueous layer was extracted with EtOAc (2×35 ml). The organic layers were combined and washed with saturated NaHCO₃ (1×15 ml), water (1×15 ml), and brine (1×15 ml), dried over MgSO₄, filtered and concentrated to an oil. The crude product was purified by flash column chromatography (95:5; hexanes: ethyl acetate) to give the title compound (0.41 g) as a solid: ¹H NMR (CDCl₃) δ1.29 (t, J=7.5 Hz, 3 H), 1.53 (s, 9 H), 2.91 (q, J=7.6 Hz, 2 H), 7.40 (br s, 1H), 7.81 (d, J=8.6 Hz, 1 H), 7.87 (d, J=8.8 Hz, 1 H).

Step B: 2-t-Butoxycarbonylamino-5-aminomethyl-6-ethylpyridine

The title compound was prepared from 2-t-butoxycarbonylamino-5-cyano-6-ethylpyridine (0.405g, 1.64 mmol) using the procedure of EXAMPLE V, Step C', as an oil (0.326 g): ¹H NMR (CDCl₃) δ1.23 (t, J=7.5 Hz, 3 H), 1.48 (br s, 2H), 1.51 (s, 9 H), 2.72 (q, J=7.5 Hz, 2 H), 3.84 (s, 2H), 7.20 (br s, 1H), 7.58 (d, J=8.4 Hz, 1 H), 7.69 (d, J=8.4 Hz, 1 H).

Step C: 3-Benzylsulfonylamino-6-methyl-1-(2-t-butoxycarbonylamino-6-ethyl-5-methylenecarboxamidomethylpyridinyl)-2-pyridinone DCC (50 mg, 0.242 mmol) was added to a stirred solution of 3-benzylsulfonylamino-6-methyl-1-methylenecarboxy-2-pyridinone (79 mg, 0.235 mmol) and 2-t-butoxycarbonylamino-6-ethyl-5-methylaminopyridine (60 mg, 0.239 mmol) in methylene chloride (2 ml). After 16 h the reaction was filtered through celite and evaporated in vacuo to afford a pale yellow resin. The crude product was purified by flash column chromatography on silica (ethyl acetate/hexanes gradient, 60%–70% ethyl acetate) to give after trituration with ethyl acetate and hexanes the title compound (69 mg, 50.7%) as a white solid: ¹H NMR (CDCl₃) δ1.18 (t, J=7.5 Hz, 3 H), 1.49 (s, 9 H), 2.43 (s, 3 H), 2.68 (q, J=7.5 Hz, 2 H), 4.08 (br s, 1 H), 4.21 (s, 2 H), 4.38 (d, J=5.5 Hz, 2 H), 4.47 (s, 2 H), 6.05 (d, J=7.7 Hz, 1 H), 7.11–7.13 (m, 4 H), 7.18–7.21 (m, 2 H), 7.39 (d, J=7.7 Hz, 1 H), 7.52 (d, J=8.4 Hz, 1 H), 7.62 (d, J=8.4 Hz, I H), 8.30 (br s, 1 H).

Step D: 3-Benzylsulfonylamino-6-methyl-1-(2-amino-6-ethyl-5-methylenecarboxamidomethylpyridinyl)-2-pyridinone A solution of 3-benzylsulfonylamino-6-methyl-1-(2-t-butoxycarbonylamino-6-ethyl-5-methylenecarboxamidomethylpyridinyl)-2-pyridinone (69 mg, 0.121 mmol) in ethyl acetate was cooled to –78° C. HCl gas was bubbled through solution for approximately 8 min and warmed to 0° C. After 2 h the reaction solution was degassed with Argon and was evaporated in vacuo. Ethyl acetate was added and solution was again evaporated in vacuo to a solid. Triturafion with ethyl acetate and subsequent filtration gave the title compound (38.3 mg, 62.5%) as a tan solid: ¹H NMR (CD₃OD) δ1.30 (t, J=7.6 Hz, 3 H), 2.32 (s, 3 H), 2.85 (q, J=7.6 Hz, 2 H), 4.13 (s, 2 H), 4.35 (d, J=5.7 Hz, 2 H), 4.83 (s, 2 H), 6.15 (d, J=7.7 Hz, 1 H), 6.82 (d, J=9.0 Hz, 1 H), 6.95 (d, J=9.3 Hz, 1 H), 7.25–7.32 (m, 5 H), 7.93 (dd, J=9.2 and 2.0 Hz, 2 H), 8.74 (br m, 1 H); MS (FAB) 470 (M+1)⁺.

EXAMPLE XXXI

Preparation of 2-Cyclohexylethylamino-6-methyl-1-(2-amino-6-methyl-5-methylenecarboxamidomethylpyridinyl)-2-pyridinone

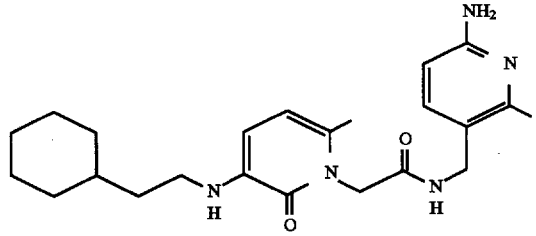

Step A: 2-Cyclohexylethylamino-6-methyl-1-(2-t-butoxycarbonylamino-6-methyl-5-methylenecarboxamidomethylpyridinyl)-2-pyridinone To a solution of cyclohexylacetaldehyde (25.9 mg, 0.206 nunol) and 2-amino-6-methyl-1-(2-t-butoxycarbonylamino-6-methyl-5-methylenecarboxamidomethylpyridinyl)-2-pyridinone (75 mg, 0.187 mmol) in methanol (5 ml) was added aluminum foil (37.8 mg, 1.40 mmol) and mercury(II) chloride (5.1 mg, 0.0187 mmol). After 16 h the reaction was filtered and concentrated in vacuo. The residue was dissolved in EtOAc, washed with a 5% solution of sodium potassium tartrate (2×20 ml)) and brine (1×20 ml). The organic layer was dried (Na₂SO₄) and concentrated in vacuo. The residue was purified by flash column chromatography on silica (eluting with 1.5:1 EtOAc:CHCl₃) to give the title compound (56 mg, 59%): ¹H NMR (400 MHz, CDCl₃) δ 0.91–1.00 (m, 2

H), 1.13–1.22 (m, 3 H), 1.35–1.43 (m, 1 H), 1.50 (s, 9 H), 1.51–1.57 (m, 3 H), 1.62–1.77 (m, 4 H), 2.35 (s, 3 H), 2.36 (s, 3 H), 3.04–3.08 (m, 2 H), 4.33 (d, J=5.8 Hz, 2 H), 4.59–4.67 (m, 1 H), 4.75 (br s, 2 H), 6.05 (d, J=7.8 Hz, 1 H), 6.15 (d, J=7.5 Hz, 1 H), 7.11–7.20 (m, 2 H), 7.38 (d, J=8.4 Hz, 1 H), 7.65 (d, J=8.4 Hz, 1 H).

Step B: 2-Cyclohexylethylamino-6-methyl-1-(2-amino-6-methyl-5-methylenecarboxamidomethylpyridinyl)-2-pyridinone A solution of 2-cyclohexylethylamino-6-methyl-1-(2-t-butoxycarbonylamino-6-methyl-5-methylenecarboxamidomethyl-pyridinyl)-2-pyridinone (56 mg, 0.109 mmol) in EtOAc (35 ml) at 0° C., was saturated with HCl gas. This solution was warmed to room temperature and after 30 min the solution was concentrated in vacuo. The residue was partitioned between EtOAc and 5% aqueous NaOH. The EtOAc layer was washed with brine, dried Na$_2$SO$_4$) and concentrated in vacuo. The crude product was purified by flash column chromatography on silica (eluting with 1.5% MeOH/chloroform saturated with ammonia) to give the title compound as a colorless solid (25 mg, 56%): $^1$H NMR (400 MHz, CDCl$_3$) δ0.93–0.99 (m, 2H), 1.16–1.25 (m, 3H), 1.33–1.44 (m, 1H), 1.48–1.60 (m, 3H), 1.63–1.80 (m, 4H), 2.31 (s, 3H), 2.35 (s, 3H), 3.05 (dd, J=13.0 and 7.14 Hz, 2H), 4.27 (d, J =5.7 Hz, 2H), 4.32 (br s, 2H), 4.63 (br t, 1H), 4.74 (s, 2H), 6.03 (d, J=7.9 Hz, 1H), 6.14 (d, J=7.3 Hz, 1H), 6.28 (d, J=8.2 Hz, 1H), 6.95 (br d, 1H), 7.24 (d, J=6.9 Hz, 1H); MS (FAB) 412 (M+1)$^+$.

EXAMPLE XXXII
Preparation of 3-Benzylsulfonylamino-6-cyclopropyl-1-(2-amino-6-methyl-5-methylenecarboxamidomethylpyridinyl)-2-pyridinone Solid 6-cyclopropyl-3-nitro-2-(1H)-pyridinone (1.4 g, 7.78 mmol) was added in small portions to a suspension of sodium hydride (260 mg, 10.8 mmol) in THF (30 ml) at room temperature. After stirring the resulting solution for 20 min, tert-butylbromoacetate (4 ml, 27 mmol) was added. The mixture was stirred for an additional 30 min. then heated at 55° C. for 15 hrs. After cooling to room temperature the THF was evaporated in vacuo and ice carefully added to the residue to destoy any excess sodium hydride. The resulting miture was extracted with 2:1:1 ethyl acetate:ether:chloroform and the extracts dried over magnesium sulfate. Filtration and evaporation of the filtrate gave a yellow oil as a 3:1 mixture of N and O-alkylated products respectively. Flash column chromatography eluting with 1:1 hexane/ethyl acetate gave 1.59 g of the title compound as a yellow crystalline solid: $^1$H NMR (CDCl$_3$) δ0.94 (m, 2 H), 1.18 (m, 2 H), 1.49 (s, 9 H), 1.79 (m, 1 H), 5.04 (s, 2 H), 6.10 (d, J=8.1 Hz, 1 H), 8.33 (d, J=8.1 Hz, 1 H).

Step D: 3-Amino-6-cyclopropyl-1-(t-butyl-methylenecarboxy)-2-pyridinone

A mixture of 3-nitro-6-cyclopropyl-1-(t-butyl-methylene-carboxy)-2-pyridinone (760 mg, 2.58 mmol) and platinum oxide (250 mg) in ethanol (30 ml) was stirred at 0° C. under an atmosphere of hydrogen for 3 hours. Following removal of most of the catalyst by filtration through a bed of Celite, the filtrate was concentrated and the rsidue purified by flash column chromatography eluting with 2:1 hexane/ethyl acetate. This yielded 506 mg of product as a very viscous orange gum: $^1$H NMR (CDCl$_3$) δ0.67 (m, 2 H), 0.89 (m, 2 H), 1.49 (s, 9 H), 1.63 (m, 1 H), 4.07 (br s, 2 H), 4.99 (s, 2 H), 5.91 (dd, J=1.2 and 7.4 Hz, 1 H), 6.47 (d, J=7.4 Hz, 1 H).

Step E: 3-Benzylsulfonylamino-6-cyclopropyl-1-(t-butyl-methylenecarboxy)-2-pyridinone

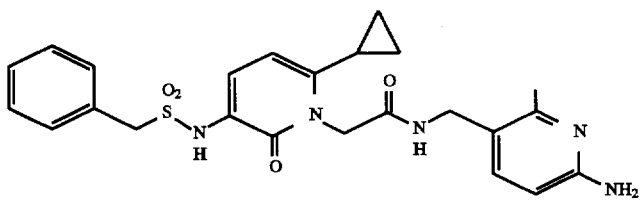

Step A: β-N,N-Dimethylaminoethenylcyclopropyl ketone
A mixture of cyclopropyl methyl ketone (5.88 ml, 59 mmol) and N,N-dimethylformaldehyde dimethyl acetal (7.83 ml, 59 mmol) was heated in the presence of a catalytic quantity of p-toluenesulfonic acid for 48 hours. The resulting crude sample of the title compound (a pale yellow oil) was used in subsequent reactions without further purification: $^1$H NMR (CDCl$_3$) δ0.74 (m, 2 H), 1.00 (m, 2 H), 1.75 (m, 1 H), 3.48 (s, 3 H), 3.50 (s, 3 H), 5.20 (d, 1 H), 7.55 (d, 1 H).

Step B: 6-Cyclopropyl-3-nitro-2-(1H)-pyridinone
A mixture of crude β-N,N-dimethylaminoethenylcyclopropyl ketone (12 g, <86 mmol), nitroacetamide (9 g, 86 mmol) and aqueous piperidinium acetate (10 ml) [prepared from glacial acetic acid (42 ml), water (100 ml) and piperidine (72 ml)] was stirred at room temperature overnight. Following dilution with water (20 ml), the yellow precipitate was isolated via filtration and drying in vacuo to yield 5.30 g of the title compound: $^1$H NMR (CDCl$_3$) δ1.15 (m, 2 H), 1.36 (m, 2 H), 2.10 (m, 1 H), 6.02 (br d, J=8.0Hz, 1 H), 8.41 (d, J=8.0 Hz, 1 H).

Step C: 3-Nitro-6-cyclopropyl-1-(t-butyl-methylenecarboxy)-2-pyridinone

The title compound was prepared from 3-amino-6-cyclopropyl-1-(t-butyl-methylenecarboxy)-2-pyridinone according to the procedure of EXAMPLE V, Step D: $^1$H NMR (CDC13) δ0.76 (m, 2 H), 1.01 (m, 2 H), 1.52 (s, 9 H), 1.68 (m, 1 H), 4.31 (s, 2 H), 4.98 (s, 2 H), 5.98 (d, J=7.7 Hz, 1 H), 7.25–7.34 (m, 6 H).

Step F: 3-Benzylsulfonylamino-6-cyclopropyl-1-methylenecarboxy-2-pyridinone

The title compound was prepared from 3-benzylsulfonyl-amino-6-cyclopropyl-1-(t-butyl-methylenecarboxy)-2-pyridinone according to the procedure of EXAMPLE V, Step E: $^1$H NMR (CDCl$_3$) δ0.77 (m, 2 H), 1.03 (m, 2 H), 1.74 (m, 1 H), 4.36 (s, 2 H), 5.06 (s, 2 H), 6.04 (d, J=7.7 Hz, 1 H), 7.30–7.39 (m, 6 H).

Step G: 3-Benzylsulfonylamino-6-cyclopropyl-1-(2-amino-6-methyl-5-methylenecarboxamidomethylpyridinyl)-2-pyridinone The title compound was prepared from 3-benzylsulfonyl-amino-6-cyclopropyl-1-methylenecarboxy-2-pyridinone and 2-t-butoxycarbonylamino-6-methyl-5-methylaminopyridine essentially according to the procedure of EXAMPLE V, Step F: $^1$H NMR (CD$_3$OD) δ0.77 (m, 2 H), 0.99 (m, 2 H), 1.82 (m, 1 H), 2.51 (s, 3 H), 4.33 (s, 2 H), 4.44

(s, 2 H), 5.03 (s, 2 H), 6.11 (d, J=7.9 Hz, 1 H), 6.79 (d, J=9.1 Hz, 1 H), 7.26–7.33 (m, 6 H), 7.87 (d, J=9.1 Hz, 1 H); MS (FAB) 482 (M+1)⁺.

EXAMPLE XXXIII

Preparation of 3-Benzylsulfonylamino-6-propyl-1-(2-amino-6-methyl-5-methylenecarboxamidomethylpyridinyl)-2-pyridinone

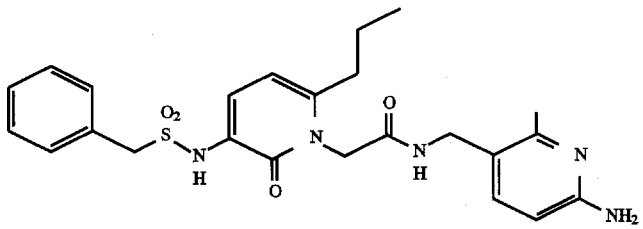

Step A: 3-Amino-6-propyl-2-(1H)-pyridinone

A mixture of 6-cyclopropyl-3-nitro-2-(1H)-pyridinone (2 g, 13.3 mmol) and 10% palladium on carbon (600 mg) in ethyl acetate (100 ml) was stirred at room temperature under an atmosphere of hydrogen overnight. The catalyst was removed by filtration through a bed of Celite and the filtrate concentrated to yield 1.63 g of product as a white microcrystalline solid. ¹H NMR (CDCl₃) δ0.94 (t, J=7.3 Hz, 3 H), 1.67 (m, 2 H), 2.49 (t, J=7.5 Hz, 2 H), 4.00 (br s), 5.88 (d, J=7.1 Hz, 1 H), 6.59 (d, J=7.1 Hz, 1 H).

Step B: 3-Benzyloxycarbonylamino-6-propyl-2-(1H)-pyridinone

Benzyl chloroformate (1.8 ml, 12.6 mmol) was added to a solution of 3-amino-6-propyl-2-(1H)-pyridinone (1.63 g, 10.8 mmol) in a mixture of dioxane (25 ml) and 1N NaOH at 0° C. Within minutes a white precipitate formed. The reaction mixture was stirred at the same temperature for 1 hr then at room temperature for an additional hour. The reaction mixture was diluted with water and extracted with ethyl acetate, then methylene chloride. Each extract was washed with brine then combined and dried over magnesium sulfate. Removal of the solvents in vacuo gave a yellow semi-solid which was a mixture of starting material and product. This was redissolved in a mixture of dioxane (24 ml) and 10% aqueous sodium bicarbonate (12 ml) and cooled to 0° C. Benzyl chloroformate (1.5 ml, 10.5 mmol) was once again added and after stirring for 30 min, the reaction mixture was allowed to stir at room temperature for 3 h. After dilution with water, the precipitate was filtered off and washed thoroughly, first with water and then with ether. Drying gave 2.64 g of the title compound as a white powder: ¹H NMR (CDCl₃) δ0.96 (t, J=7.3 Hz, 3 H), 1.68 (m, 2 H), 2.52 (t, J=7.5 Hz, 2 H), 5.22 (s, 2 H), 6.07 (d, J=7.5 Hz, 1 H), 7.34–7.43 (m, 4 H), 7.68 (s, 1 H), 8.05 (brd,J=5.3Hz, 1H).

Step C 3-Benzyloxycarbonylamino-6-propyl-1-(t-butyl-methylenecarboxy)-2-pyridinone Solid 3-benzyloxycarbonylamino-6-propyl-2-(1H)-pyridinone (2.64 g, 9.3 mmol) was added in small portions to a suspension of sodium hydride (269 mg, 11.2 mmol) in THF (30 ml) at 0° C. The reaction mixture was the stirred at room temperature for 20 min by which time an almost completely homogeneous solution had been obtained. Tert-butyl-bromoacetate (2.2 ml, 14.9 mmol) was then added. Within minutes a white precipitate started forming. Stirring was continued overnight, then the THF was evaporated in vacuo. Ice was carefully added to the residue to destoy any excess sodium hydride. Brine was added and the resulting miture was extracted with 2:1:1 ethyl acetate/ether/chloroform and the combined extracts were dried over magnesium sulfate. Filtration and evaporation of the filtrate gave a cream solid which was purified by flash column chromatography eluting with 3:1:1 hexane/chloroform/ethyl acetate. This gave 2.38 g of the title compound as a white crystalline solid: ¹H NMR (CDCl3) δ 1.00 (t, J=7.3 Hz, 3 H), 1.48 (s, 9 H), 1.64 (m, 2 H), 2.46 (t, J=7.6 Hz, 2 H), 4.72 (s, 2 H), 5.20 (s, 2 H), 6.08 (d, J=7.7 Hz, 1 H), 7.31–7.40 (m, 4 H), 7.77 (s, 1 H), 7.97 (br d, J =7.0 Hz, 1 H).

Step D: 3-Amino-6-propyl-1-(t-butyl-methylenecarboxy)-2-pyridinone

3-Benzyloxycarbonylamino-6-propyl-1-(t-butyl-methylenecarboxy)-2-pyridinone (2.38 g, mmol) was dissolved in a 1:1 mixture of ethyl acetate and ethanol (100 ml) and then stirred in the presence of 20% palladium hydroxide on carbon (800 mg) under an atmosphere of hydrogen for 2 h. The catalyst was removed by filtration through Celite and the filtrate concentrated to give the title compound as an orange oil (1.65 g): ¹H NMR (CDCl₃) δ0.98 (t, J=7.3 Hz, 3 H), 1.47 (s, 9 H), 1.57 (m, 2 H), 2.40 (t, J=7.7 Hz, 2 H), 4.73 (s, 2 H), 5.91 (d,J=7.3 Hz, 1 H), 6.55 (d, J=7.3 Hz, 1 H).

Step E: 3-Benzylsulfonylamino-6-propyl-1-(t-butyl-methylene-carboxy)-2-pyridinone The title compound was prepared from 3-amino-6-propyl-1-(t-butyl-methylenecarboxy)-2-pyridinone according to the procedure of EXAMPLE V, Step D:

Step F: 3-Benzylsulfonylamino-6-propyl-1-methylenecarboxy-2-pyridinone

The title compound was prepared from 3-benzylsulfonylamino-6-propyl-1-(t-butyl-methylenecarboxy)-2-pyridinone according to the procedure of EXAMPLE V, Step E:

Step G: 3-Benzylsulfonylamino-6-propyl-1-(2-amino-6-methyl-5-methylenecarboxamidomethylpyridinyl)-2-pyridinone The title compound was prepared from 3-benzylsulfonylamino-6-propyl-1-methylenecarboxy-2-pyridinone and 2-t-butoxycarbonylamino -6-methyl-5-methylaminopyridine essentially according to the procedure of EXAMPLE V, Step F: ¹H NMR (CDCl₃) δ 1.01 (t, J=7.3 Hz, 3 H), 1.63 (m, 2 H), 2.51 (s, 3 H), 2.57 (m, 2H), 4.32 (d, J=5.7 Hz, 2H), 4.44 (s, 2H), 4.78 (s, 2 H), 6.14 (d, J =7.7 Hz, 1 H), 6.79 (d, J =9.0 Hz, 1 H), 7.26–7.34 (m, 6H), 7.89 (d, J=9.0 Hz, 1 H).

EXAMPLE XXXIV

Preparation of 3-Benzyloxycarbonylmethylamino-6-methyl-1-(2-amino-6-methyl-5-methylenecarboxamidomethylpyridinyl)-2-pyridinone

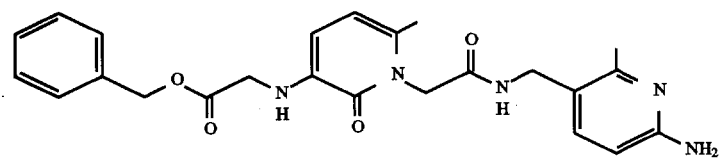

Step A: 3-Benzyloxycarbonylmethylamino-6-methyl-1-(t-butyl-methylenecarboxy)-2-pyridinone A solution of 3-amino-6-methyl-1-(t-butyl-methylenecarboxy)-2-pyridinone (1.04 g) and N,N-diisopropylethylamine (0.88 ml, 5.03 mmol) in DMF was treated at 0° C. with benzyl bromoacetate (0.80 ml, 5.03 mmol). The reaction mixture was allowed to warm gradually to room temperature and was then stirred overnight. The volatiles were removed under reduced pressure and the residue dissolved in the minimum quantity of chloroform. This solution was then partitioned between ethyl acetate and saturated sodium bicarbonate. The organic phase was separated and washed with water and then brine. Drying and removal of the solvents gave a dark yellow oil which was purified by preparative HPLC: $^1$H NMR (CDCl$_3$) δ1.47 (s, 9 H), 2.20 (s, 3 H), 3.91 (s, 2 H), 4.76 (s, 2 H), 5.20 (s, 2 H), 5.98 (d, J=7.4 Hz, 1 H), 6.09 (d, J=7.4 Hz, 1 H), 7.35 (m, 5 H).

Step B: 3-Benzyloxycarbonylmethylamino-6-methyl-1-methylene-carboxy-2-pyridinone The title compound was prepared from 3-benzyloxycarbonyl-methylamino-6-methyl-1-(t-butyl-methylenecarboxy)-2-pyridinone according to the procedure of EXAMPLE V, Step E: $^1$H NMR (CDCl$_3$) δ2.27 (s, 3 H), 3.99 (s, 2 H), 4.81 (s, 2 H), 5.21 (s, 2 H), 6.07 (d, J=7.5 Hz, 1 H), 6.60 (d, J=7.5 Hz, 1 H), 7.35 (m, 5 H).

Step C: 3-Benzyloxycarbonylmethylamino-6-methyl-1-(2-amino-6-methyl-5-methylenecarboxamidomethyl-pyridinyl)-2-pyridinone The title compound was prepared from 3-benzyloxycarbonyl-methylamino-6-methyl-1-methylenecarboxy-2-pyridinone and 2-t-butoxy-carbonylamino-6-methyl-5-methylaminopyridine essentially according to the procedure of EXAMPLE V, Step F: $^1$H NMR (CDCl$_3$) δ2.32 (s, 3 H), 2.36 (s, 3H), 3.91 (d, J=6.2 Hz, 2 H), 4.26 (d, J=5.7 Hz, 2 H), 4.73 (m, 2 H), 5.20 (m, 2 H), 6.00 (d, J=7.3 Hz, I H), 6.09 (d, J=7.3 Hz, 1 H), 6.29 (d, J=8.6 Hz, 1 H), 7.35 (m, 5 H); MS (FAB) 450 (M+1)$^+$.

EXAMPLE XXXV

Preparation of 3-(Ethyl L-phenylalanyl)-6-methyl-1-(2-amino-6-methyl-5-methylenecarboxamidomethylpyridinyl)-2-pyridinone

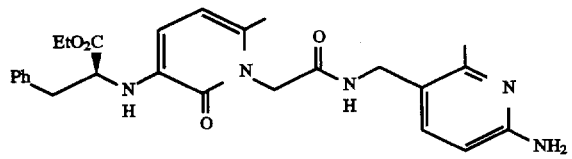

Step A: 3-(Ethyl L-phenylalanyl)-6-methyl-1-(t-butyl-methylene-carboxy)-2-pyridinone A solution of ethyl (R)-2(trifluoromethylsulfonyloxy)-3-phenylpropionate (1.7 g, 4 mmol) in methylene chloride (5 ml) was added at room temperature to a solution of 3-amino-6-methyl-1-(t-butyl-methylenecarboxy)-2-pyridinone (601 mg, 2.5 mmol) and N,N-diisopropylethylamine (0.7 ml, 4 mmol) in methylene chloride (10 ml). After stirring for 88 hours the reaction mixture was washed with saturated sodium bicarbonate and dried over magnesium sulfate. Filtration, evaporation of the solvents, and chromatography on silica of the residue eluting with 7:3 hexane:ethyl acetate, gave the title compound as a yellow oil (740 mg).

Step B: 3-(Ethyl L-phenylalanyl)-6-methyl-1-methylenecarboxy-2-pyridinone

The title compound was prepared from 3-(ethyl L-phenylalanyl)-6-methyl-1-(t-butyl-methylenecarboxy)-2-pyridinone according to the procedure of EXAMPLE V, Step E:

Step C: 3-(Ethyl L-phenylalanyl)-6-methyl-1-(2-amino-6-methyl-5-methylenecarboxamidomethylpyridinyl)-2-pyridinone The title compound was prepared from 3-(ethyl L-phenylalanyl)-6-methyl-1-methylenecarboxy-2-pyridinone and 2-t-butoxycarbonylamino-6-methyl-5-methylaminopyridine essentially according to the procedure of EXAMPLE V, Step F: $^1$H NMR (CDCl$_3$) δ 1.16 (t, J=7.1 Hz, 3H), 2.24 (s, 3 H), 2.49 (s, 3H), 3.13 (m, 2 H), 4.09 (q, J=7.1, 13.9 Hz, 2 H), 4.28 (m, 2 H), 4.77 (s, 2H), 6.01 (d, J=7.5 Hz, 1 H), 6.33 (d, J=7.5 Hz, 1 H), 6.79 (d, J=9.0 Hz, 1 H), 7.22 (m, 5 H), 7.83 (d, J=9.0, 1H); MS (FAB) 478 (M+1)$^+$.

EXAMPLE XXXVI

Preparation of 3-(Ethyl D-phenylalanyl)-6-methyl-1-(2-amino-6-methyl-5-methylenecarboxamidomethylpyridinyl)-2-pyridinone

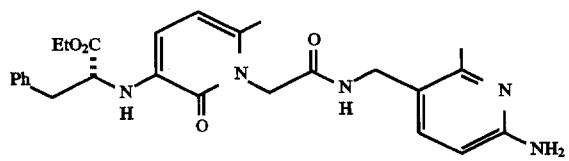

3-(Ethyl D-phenylalanyl)-6-methyl-1-(2-amino-6-methyl-5-methylenecarboxamidomethylpyridinyl)-2-pyridinone The title compound was prepared according to the procedure of EXAMPLE XXXV, employing ethyl (S)-2 (trifluoromethylsulfonyloxy)-3-phenylpropionate.

EXAMPLE XXXVII

Preparation of 3-Benzylsulfonylamino-6-cyclopropyl-1-(2-amino-5-methylenecarboxamidomethylpyridinyl)-2-pyridinone

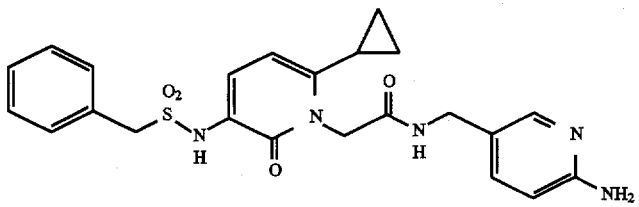

The title compound was prepared from 3-benzylsulfonyl-amino-6-cyclopropyl-1-methylenecarboxy-2-pyridinone and 2-t-butoxycarbonylamino-5-methylaminopyridine essentially according to the procedure of EXAMPLE V, Step F: $^1$H NMR (CD$_3$OD) δ0.76 (m, 2 H), 1.00 (m, 2 H), 1.83 (m, 1 H), 4.34 (s, 2 H), 4.44 (s, 2 H), 5.04 (s, 2 H), 6.13 (d, J=7.8 Hz, 1 H), 6.96 (d, J=9.0 Hz, 1 H), 7.24–7.34 (m, 6 H), 7.81 (s, 1 H), 7.90 (d, J=8.6 Hz, 1 H); MS (FAB) 468 (M+1)$^+$.

EXAMPLE XXXVIII

Preparation of 3-(4-Chlorobenzyl)sulfonylamino-6-cyclopropyl-1-(2-amino-6-methyl-5-methylenecarboxamidomethylpyridinyl)-2-pyridinone

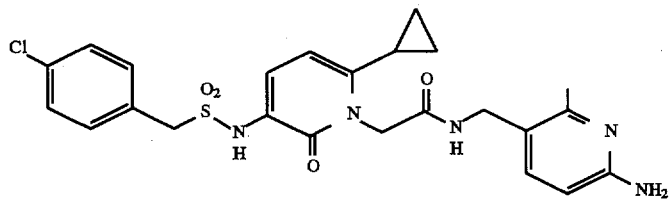

The title compound was prepared from 3-amino-6-cyclopropyl-1-(t-butyl-methylenecarboxy)-2-pyridinone, 4-chlorobenzylsulfonyl chloride and 2-t-butoxycarbonylamino-6-methyl-5-methylaminopyridine essentially according to the procedure of EXAMPLE V, Steps D–F: $^1$H NMR (CD$_3$OD) δ0.77 (m, 2 H), 1.00 (m, 2 H), 1.81 (m, 1 H), 2.52 (s, 3 H), 4.33 (s, 2 H), 4.43 (s, 2 H), 5.03 (s, 2 H), 6.09 (d, J=7.7 Hz, 1 H), 6.77 (d, J=9.1 Hz, 1 H), 7.20 (d, J=8.5 Hz), 7.25 (d, J=8.5 Hz), 2 H), 7.33 (d, J=7.7 Hz, 1 H), 7.89 (d, J=9.1 Hz, 1 H); MS (FAB) 516 (M+1)$^+$.

EXAMPLE XXXIX

Preparation of 3-(4-Chlorobenzyl)sulfonylamino-6-cyclopropyl-1-(2-amino-5-methylenecarboxamidomethylpyridinyl)-2-pyridinone

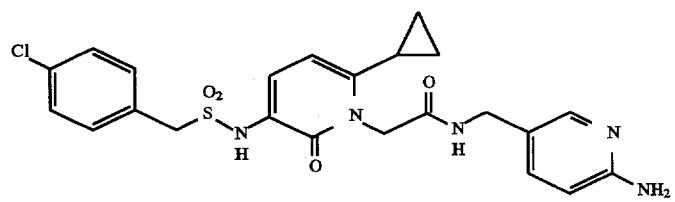

Step A: 3-(4-Chlorobenzyl)sulfonylamino-6-cyclopropyl-1-(2-t-butoxycarbonylamino-5-methylenecarboxamidomethylpyridinyl)-2-pyridinone The title compound was prepared from 3-(4-chlorobenzyl)-sulfonyl-amino-6-cyclopropyl-1-methylenecarboxy-2-pyridinone and 2-t-butoxycarbonylamino-5-methylaminopyridine essentially according to the procedure of EXAMPLE V, Steps D–F: $^1$H NMR (CD$_3$OD) δ0.78 (m, 2 H), 1.01 (m, 2H), 1.83 (m, 1 H), 4.35 (s, 2H), 4.43 (s, 2H), 5.05 (s, 2H), 6.10 (d, J=7.7 Hz, 1 H), 6.95 (d, J=9.3 Hz, 1 H), 7.22 (m, 4 H), 7.35 (d, J=7.7 Hz, 1 H), 7.81 (s, 1 H), 7.91 (dd, J=1.8 and 9.3 Hz, 1 H); MS (FAB) 502 (M+1)$^+$

EXAMPLE XL

Preparation of 3-Cyclohexylmethylsulfonylamino-6-cyclopropyl-1-(2-amino-6-methyl-5-methylenecarboxamidomethylpyridinyl)-2-pyridinone

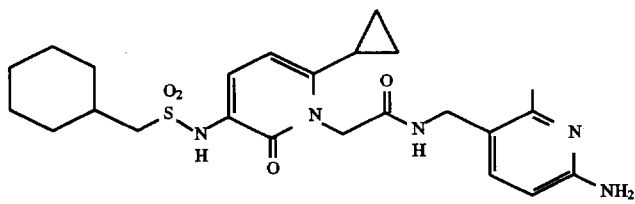

The title compound was prepared from 3-amino-6-cyclopropyl-1-(t-butyl-methylenecarboxy)-2-pyridinone, cyclohexylmethylsulfonyl chloride and 2-t-butoxycarbonylamino-6-methyl-5-methylaminopyridine essentially according to the procedure of EXAMPLE V, Steps D–F: $^1$H NMR (CD$_3$OD) δ2.51 (s, 3 H), 2.97 (d, J=5.8Hz, 2 H), 4.31 (s, 2 H), 5.07 (s, 2 H), 6.20 (d, J=7.7 Hz, 1 H), 6.78 (d, J=9.0 Hz, 1 H), 7.46 (d, J=7.7 Hz, 1 H), 7.88 (d, J=9.0 Hz, 1 H); MS (FAB) 488 (M+1)$^+$.

EXAMPLE XLI
Preparation of 3-Cyclohexylmethylsulfonylamino-6-cyclopropyl-1-(2-amino-5-methylenecarboxamidomethylpyridinyl)-2-pyridinone

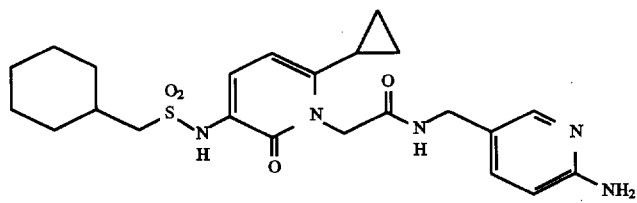

The title compound was prepared from 3-cyclohexylmethylsulfonylamino-6-cyclopropyl-1-methylenecarboxy-2-pyridinone and 2-t-butoxycarbonylamino-5-methylaminopyridine essentially according to the procedure of EXAMPLE V, Step, F: $^1$H NMR (CD$_3$OD) δ2.98 (d, J=5.8 Hz, 2 H), 4.32 (s, 2 H), 5.09 (s, 2 H), 6.21 (d, J=7.8 Hz, 1 H), 6.97 (d, J=9.3 Hz, 1 H), 7.45 (d, J=7.8 Hz, 1 H), 7.81 (s, 1 H), 7.89 (d, J=1.8 Hz, 1 H) 7.92 (d, J=1.8 Hz, 1 H); MS (FAB) 474 (M+1)$^+$

EXAMPLE XLII
Preparation of 3-Cyclohexylmethylsulfonylamino-6-methyl-1-(2-amino-6-methyl-5-methylenecarboxamidomethyylpyridinyl)-2-pyridinone

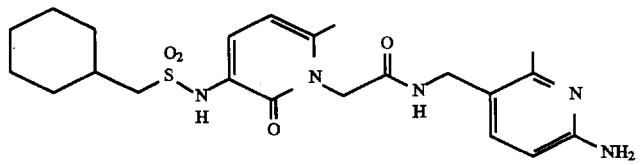

The title compound was prepared from 3-amino-6-methyl-1-(t-butyl-methylenecarboxy)-2-pyridinone, cyclohexylmethylsulfonyl chloride and 2-t-butoxycarbonylamino-6-methyl-5-methylaminopyridine essentially according to the procedure of EXAMPLE V, Steps D–F: $^1$H NMR (CD$_3$OD) δ0.99–1.91 (m, 10 H), 2.33 (s, 3 H), 2.51 (s, 3 H), 3.03 (d, J=6.6 Hz, 2 H), 4.30 (s, 2 H), 6.23 (d, J=7.5 Hz, 1 H), 6.80 (d, J=9.0 Hz, 1 H), 7.44 (d, J=7.5 Hz, 1 H), 7.86 (d, J=9.0 Hz, 1 H); MS (FAB) 462 (M+1)$^+$.

EXAMPLE XLIII
Preparation of 3-Cyclohexylmethylsulfonylamino-6-methyl-1-(2-amino-5-methylenecarboxamidomethylpyridinyl)-2-pyridinone

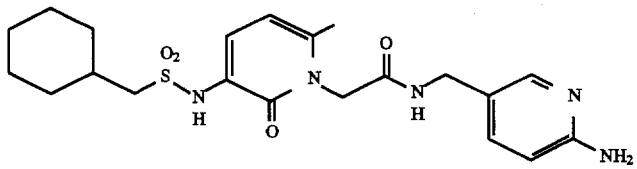

The title compound was prepared from 3-cyclohexylmethyl-sulfonylamino-6-methyl-1-methylenecarboxy-2-pyridinone and 2-t-butoxycarbonylamino-5-methylaminopyridine essentially according to the procedure of EXAMPLE V, Step F: $^1$H NMR (CD$_3$OD) δ2.35 (s, 3 H), 2.97 (d, J=6.0 Hz, 2 H), 4.31 (s, 2 H), 4.84 (s, 2 H), 6.24 (d, J=7.6 Hz, 1 H), 6.98 (d, J=9.1 Hz, 1 H), 7.44 (d, J=7.6 Hz, 1 H), 7.79 (s, 1 H), 7.90 (dd, J=2.1 and 9.1 Hz, 1 H); MS (FAB) 448 (M+1)$^+$.

EXAMPLE XLIV
Preparation of 3-(2-Cyclohexylethyl)sulfonylamino-6-methyl-1-(2-amino-6-methyl-5-methylenecarboxamidomethylpyridinyl)-2-pyridinone

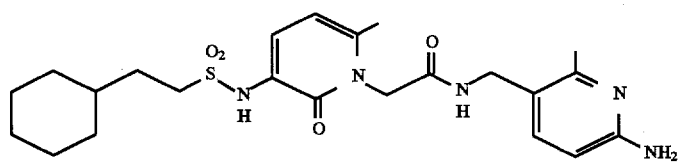

The title compound was prepared from 3-amino-6-methyl-1-(t-butyl-methylenecarboxy)-2-pyridinone, 2-cyclohexylethylsulfonyl chloride and 2-t-butoxycarbonylamino-6-methyl-5-methylaminopyridine essentially according to the procedure of EXAMPLE V, Steps D–F: $^1$H NMR (CD$_3$OD) δ2.34 (s, 3 H), 2.51 (s, 3 H), 3.09 (m, 2 H), 4.31 (m, 2 H), 4.82 (s, 2 H), 6.23 (d, J=7.6 Hz, 1 H), 6.81 (d, J=9.0 Hz, 1 H), 7.45 (d, J=7.6 Hz, 1 H), 7.87 (d, J=9.0 Hz, 1 H); MS (FAB) 476 (M+1)$^+$.

EXAMPLE XLV
Preparation of 3-(2-Cyclohexylethyl)sulfonylamino-6-methyl-1-(2-amino-5-methylenecarboxamidomethylpyridinyl)-2-pyridinone

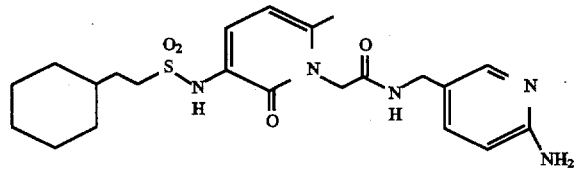

Step A: 3-Cyclohexylethylsulfonylamino-6-methyl-1-(2-t-butoxy-carbonylamino-5-methylenecarboxamidomethylpyridinyl)-2-pyridinone
The title compound was prepared from 3-cyclohexylethyl-sulfonylamino-6-methyl-1-methylenecarboxy-2-pyridinone and 2-t-butoxycarbonylamino-5-methylaminopyridine essentially according to the procedure of EXAMPLE V, Step F: $^1$H NMR (CD$_3$OD) δ2.35 (s, 3 H), 3.06–3.12 (m, 2 H), 4.32 (s, 2 H), 4.84 (s, 2 H), 6.24 (d, J=7.6 Hz, 1 H), 6.98 (d, J=9.3 Hz, 1 H), 7.46 (d, J=7.6 Hz, 1 H), 7.80 (s, 1 H), 7.90 (dd, J=2.1 and 9.3 Hz, 1 H); MS (FAB) 462 (M+1)$^+$.

EXAMPLE XLVI
Preparation of (+/−)-3-(2-tetrahydropyranylmethylsulfonylamino)-6-methyl-1-(2-amino-6-methyl-5-methylenecarboxamidomethylpyridinyl)-2-pyridinone

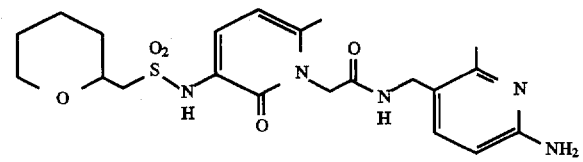

The title compound was prepared from 3-amino-6-methyl-1-(t-butyl-methylenecarboxy)-2-pyridinone, 2-tetrahydropyranylmethyl-sulfonyl chloride and 2-t-butoxycarbonylamino-6-methyl-5-methylaminopyridine essentially according to the procedure of EXAMPLE V, Steps D–F: $^1$H NMR (CD$_3$OD) δ1.18–1.78 (m, 6 H), 2.33 (s, 3 H), 2.50 (s, 3 H), 3.25 (m, 3 H), 3.80 (d, J=10.8 Hz, 2 H), 4.30 (s, 2 H), 4.81 (s, 2 H), 6.22 (d, J=7.6 Hz, 1 H), 6.78 (d, J=9.0 Hz, 1 H), 7.45 (d, J=7.6 Hz, 1 H), 7.85 (d, J=9.0 Hz, 1 H); MS (FAB) 464 (M+1)$^+$.

EXAMPLE XLVII
Preparation of 3-Butylsulfonylamino-6-methyl-1-(2-amino-6-methyl-5-methylenecarboxamidomethyylpyridinyl)-2-pyridinone

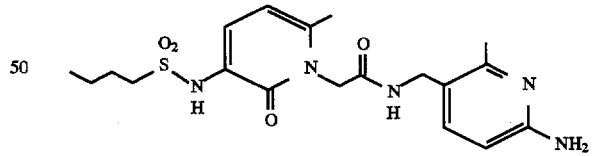

The title compound was prepared from 3-amino-6-methyl-1-(t-butyl-meffiylenecarboxy)-2-pyridinone, 3-butylsulfonyl chloride and 2-t-butoxycarbonylamino-6-methyl-5-methylaminopyridine essentially according to the procedure of EXAMPLE V, Steps D–F: $^1$H NMR (CD$_3$OD) δ0.89 (t, J=7.3 Hz, 3 H), 1.38 (m, 2 H), 1.72 (m, 2 H), 2.33 (s, 3 H), 2.50 (s, 3 H), 3.08 (m, 2 H), 4.30 (s, 2 H), 4.82 (s, 2 H), 6.23 (d, J=7.6 Hz, 1 H), 6.80 (d, J=9.2 Hz, 1 H), 7.45 (d, J=7.6 Hz, 1 H), 7.86 (d, J=9.2 Hz, 1 H); MS (FAB) 422 (M+1)$^+$.

EXAMPLE XLVIII
Preparation of 3-(3-Methyl-1-butylsulfonylamino)-6-methyl-1-(2-amino-6-methyl-5- methylenecarboxamidomethylpyridinyl)-2-pyridinone

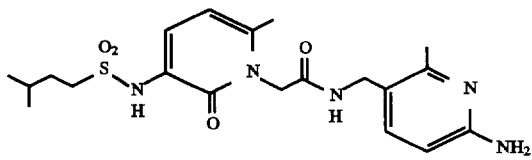

The title compound was prepared from 3-amino-6-methyl-1-(t-butyl-methylenecarboxy)-2-pyridinone, 3-methyl-1-butylsulfonyl chloride and 2-t-butoxycarbonylamino-6-methyl-5-methylaminopyridine essentially according to the procedure of EXAMPLE V, Steps D–F: $^1$H NMR (CD$_3$OD) δ0.86 (d, J=4.6 Hz, 6 H), 1.63 (m, 3 H), 2.33 (s, 3 H), 2.51 (s, 3 H), 3.12 (m, 2 H), 4.30 (s, 2 H), 4.82 (s, 2 H), 6.23 (d, J=7.3 Hz, 1 H), 6.80 (d, J=9.3 Hz, 1 H), 7.45 (d, J=7.3 Hz, 1 H), 7.87 (d, J=9.3 Hz, 1 H); MS (FAB) 436 (M+1)+.

EXAMPLE IL
Preparation of 3-Pentylsulfonylamino-6-methyl-1-(2-amino-6-methyl-5-methylenecarboxamidomethylpyridinyl)-2-pyridinone

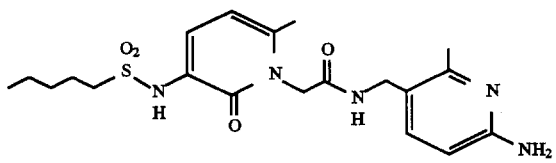

The title compound was prepared from 3-amino-6-methyl-1-(t-butyl-methylenecarboxy)-2-pyridinone, pentylsulfonyl chloride and 2-t-butoxy-carbonylamino-6-methyl-5-methylaminopyridine essentially according to the procedure of EXAMPLE V, Steps D–F: $^1$H NMR (CD$_3$OD) δ0.87 (t, J=6.8 Hz, 3 H), 1.31 (m, 4 H), 1.74 (m, 2 H), 2.34 (s, 3 H), 2.50 (s, 3 H), 3.08 (m, 2 H), 4.31 (s, 2 H), 4.83 (s, 2 H), 6.23 (d, J=7.6 Hz, 1 H), 6.79 (d, J=9.1 Hz, 1 H), 7.45 (d, J=7.6 Hz, 1 H), 7.86 (d, J=9.1 Hz, 1 H); MS (FAB) 436 (M+1)+.

EXAMPLE L
Preparation of 3-[2-(4-Morpholinoethyl)sulfonylamino]-6-methyl-1-(2-amino-6-methyl-5-methylenecarboxamidomethylpyridinyl)-2-pyridinone

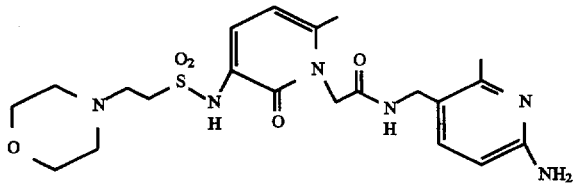

Step A: 3-Vinylsulfonylamino-6-methyl-1-(t-butyl-methylenecarboxy)-2-pyridinone
2-Chloroethylsulfonyl chloride (513 mg, 3.1 mmol) was added to a solution of 3-amino-6-methyl-1-(t-butyl-methylenecarboxy)-2-pyridinone in pyridine (50 ml) and the resulting mixture was stirred at room temperature overnight. The solvent was evaporated in vacuo and the residue was redissolved in chloroform, washed with water, dried over magnesium sulfate and evaporated in vacuo. The residue was purified by preparative HPLC to give the title compound.

Step B: 3-[2-(4-Morpholinoethyl)sulfonylamino]-6-methyl-1-(t-butyl-methylene-carboxy)-2-pyridinone
Morpholine (106 μl, 1.2 mmol) was added to a stirred solution of 3-vinylsulfonylamino-6-methyl-1-(t-butyl-methylenecarboxy)-2-pyridinone (200 mg, 0.61 mmol) in methylene chloride (50 ml). After 64 h the reaction mixture was washed with 10% sodium carbonate, dried (magnesium sulfate) and evaporated in vacuo. $^1$H NMR (CDCl$_3$) δ2.36 (s, 3 H), 2.52 (s, 3H), 3.62 (s, 4 H), 3.88 (s, 2H), 4.32 (s, 2 H), 6.35 (d, J=7.7 Hz, 1 H), 6.81 (d, J=8.8 Hz, 1 H), 7.54 (d, J=7.7 Hz, 1 H), 8.84 (d, J=8.8 Hz, 1 H); MS (FAB) 479 (M+1)+.

EXAMPLE LI
IN VITRO ASSAY FOR DETERMINING PROTEINASE INHIBITION

Assays of human α-thrombin and human trypsin were performed by the methods substantially as described in *Thrombosis Research*, Issue No. 70, page 173 (1993) by S. D. Lewis et al.

The assays were carried out at 25° C. in 0.05 M TRIS buffer pH 7.4, 0.15 M NaCl, 0.1 % PEG. Trypsin assays also contained 1 mM CaCl$_2$. In assays wherein rates of hydrolysis of a p-nitroanilide (pna) substrate were determined, a Thermomax 96-well plate reader was used was used to measure (at 405 nm) the time dependent appearance of p-nitroanline. sar-PR-pna was used to assay human a-thrombin ($K_m$=125 μM) and bovine trypsin ($K_m$=125 μM). p-Nitroanilide substrate concentration was determined from measurements of absorbance at 342 nm using an extinction coefficient of 8270 cm$^{-M-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of VO/Vi on [I] shown in equation 1.

$$V_o/V_i=1+[I]/K_i \qquad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. Compounds of Examples 1–4 inhibit human thrombin with Ki alues less than 100 nM and inhibit human trypsin with Ki values greater han 500 nM.

EXAMPLE LII

IN VIVO STUDIES TO MEASURE THROMBOTIC OCCLUSIONS

Applicants have conducted in vivo studies of the compounds claimed herein using the following rat ferric chloride assay similarly as described in Thrombosis Research, No. 60, page 269(1990) by Kurtz et al.

In the assay used to determine in vivo activity of the thrombin inhibitors or the invention, Male Sprague-Dawley rats (body weights 200–350 grams) were anesthetized with dial-urethane solution (0.1 ml/100 gm body weight i.p.), and a lateral tail vein was cannulated with a 23 gauge needle connected to a 12 inch length of PE50 tubing. The tubing was attached to a 3-way valve by a tubing adapter. Saline (control) or test compound, as appropriate, was administered via the tail vein catheter. A tracheostomy was performed with a 0.75 inch length of PE205 tubing. The right carotid artery was exposed and a 1.3 mm diameter Doppler flow probe was placed on the vessel. Body temperature was maintained at 37° C. using a heat lamp.

Rats (8–10/group) were randomized to continuous intravenous infusions of saline or test compound administered via the tail vein at a rate of 0.028 ml/min. Treatment infusions were initiated 120 min before the placement of a 3 mm square piece of Whatman No. 1 filter paper saturated with 35% $FeCl_3$ onto the exposed carotid artery distal to the flow probe. Treatment infusions were continued for an additional 60 minutes after the application of $FeCl_3$ (total infusion duration 180 minutes) if thrombotic occlusions did not occur, or were terminated 30 minutes after thrombotic occlusion of the vessel. Time to occlusion was defined as the time from application of $FeCl_3$ to thrombotic occlusion of the vessel. At the termination of the study (60 minutes after application of $FeCl_3$ in animals which did not occlude, or at 30 minutes after ffrombotic occlusion), 3 ml blood samples were drawn by cardiac puncture into 0.3 ml of 3.8% sodium citrate.

The results show that the compounds of the invention are useful in preventing thrombotic occlusions.

EXAMPLE LIII

Tablet Preparation

Tablets containing 25.0, 50.0, and 100.0 mg, respectively, of the following active compounds are prepared as illustrated below:

3-Benzylsulfonylamino-6-methyl-1-(4-methylenecarboxamidomethyl-1-amidinopiperidinyl)-2-pyridinone, 3-(2-Phenylethylamino)-6-methyl-1-(methylenecarboxamido-trans-4-aminocyclohexylmethyl)-2-pyridinone, 3-Benzylsulfonylamino-6-methyl-1-(methylenecarboxamido-trans-4-aminocyclohexylmethyl)-2-pyridinone, 3-Benzylsulfonylamino-6-methyl-1-(2-amino-5-methylenecarboxamidomethylpyridinyl)-2-pyridinone.

| TABLE FOR DOSES CONTAINING FROM 25–100 MG OF THE ACTIVE COMPOUND | | | |
|---|---|---|---|
| | Amount-mg | | |
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE LIV

An intravenous dosage form of the above-indicated active compound is prepared as follows:

| Active Compound | 0.5–10.0 mg |
|---|---|
| Sodium Citrate | 5–50 mg |
| Citric Acid | 1–15 mg |
| Sodium Chloride | 1 . 8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeial/National Formulary for 1995, published by United States Pharmacopeial Convention, Inc., Rockville, Md., copyright 1994.

What is claimed is:

1. A compound having the formula:

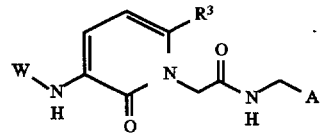

wherein W is $R^1$, $R^1OCO$, $R^1CO$, $R^1SO_2$, $(R^1)_m(CH_2)_n NH_qCO$, where n is 0–4, m is 1 or 2, and q is 0 or 1, with the proviso that where n is 1–4,q is 1 and m is 1, and where n is 0, m is 1 or2, and q is 0or 1, and where n is 0, m is 2and q is 0, $R^1$ can be the same or different;

$R^1$ is $R^2(CH_2)_n$, where n is 0–4, $(R^2)(OR^2)CH(CH_2)_p$, where p is 1–4, $(R^2)_2CH(CH_2)_n$, where n is 0–4 and $R^2$ can be the same or different, and wherein $(R^2)_2$ can also be a ring substituent on CH represented by $C_{3-7}$ cycloalkyl, $C_{7-12}$ bicyclic alkyl, or a 5- to 7- membered mono- or bicyclic heterocyclic ring which can be saturated or unsaturated, and which contains from one to three heteroatoms selected from the group consisting of N, O and S, and $R^2O(CH_2)_p$, wherein p is 1–4;

$R^2$ is hydrogen, phenyl, unsubstituted or substituted with one or more of $C_{1-4}$ linear or branched alkyl, $C_{1-4}$ linear or branched alkoxy, halogen, trifluoromethyl, hydroxy, COOH, or $CONH_2$, naphthyl, biphenyl, a 5- to 7- membered mono- or a 9- to 10-membered bicyclic heterocyclic ring which can be saturated or unsaturated, and which contains from one to three heteroatoms selected from the group consisting of N, O and S, COOR$^6$, C$_{1-4}$ linear or branched alkyl, C$_{3-7}$ cycloalkyl, or C$_{7-12}$ bicyclic alkyl;

R$^3$ is hydrogen, C$_{1-4}$ linear or branched alkyl, C$_{3-7}$ cycloalkyl, or trifluoromethyl;

A is chosen from one of the following Radicals:

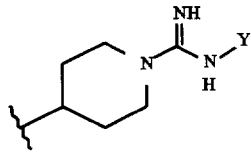

IV

Y is hydrogen, hydroxy, or CN;

R$^6$ is hydrogen, or C$_{1-4}$ linear or branched alkyl, and pharmaceutically acceptable salts thereof.

2. The compound of claim 1 wherein W is R$^1$ or R$^1$SO$_2$, and pharmaceutically acceptable salts thereof.

3. The compound of claim 2 wherein R$^1$, by itself or in R$^1$SO$_2$, is R$^2$(CH$_2$)$_n$, or (R$^2$)$_2$CH(CH$_2$)$_n$, phenyl, or (phenyl)$_2$—CH, and pharmaceutically acceptable salts thereof.

4. The compound of claim 1 wherein R$^3$ is C$_{1-4}$ linear or branched alkyl, and pharmaceutically acceptable salts thereof.

5. The compound of claim 4 wherein R$^3$ is methyl, and pharmaceutically acceptable salts thereof.

6. The compound of claim 1 wherein said radical A is Radical IV, and pharmaceutically acceptable salts thereof.

7. The compound of claim 1 selected from:

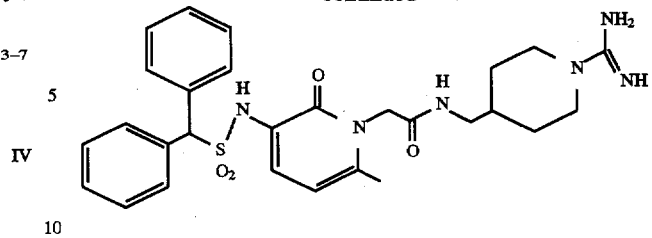

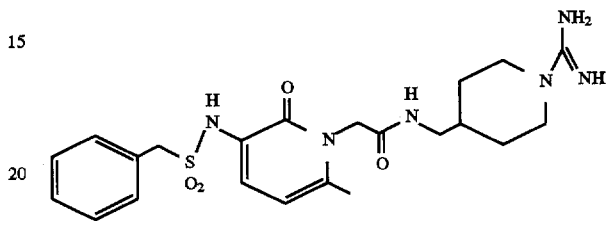

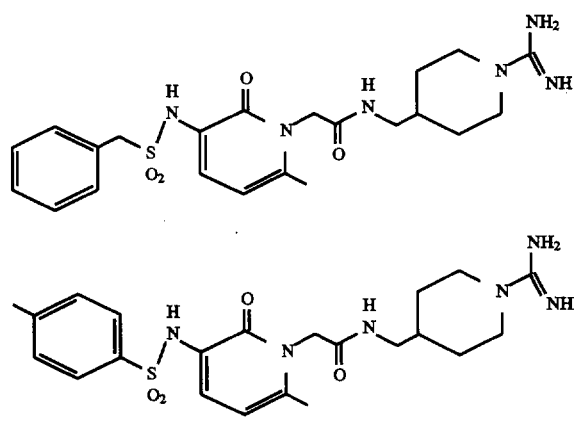

and pharmaceutically acceptable salts thereof.

8. The compound of claim 1 selected from:

and pharmaceutically acceptable salts thereof.

9. The compound of claim 1 wherein said heterocyclic group is selected from: piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl.

10. A composition for inhibiting thrombin in blood comprising a compound of claim 1 and a pharmaceutically acceptable carrier.

11. A method for inhibiting thrombin in blood comprising adding to the blood a composition of claim 10.

12. A method for inhibiting formation of blood platelet aggregates in blood comprising adding to the blood a composition of claim 10.

13. A method for inhibiting thrombus formation in blood comprising adding to the blood a composition of claim 10.

* * * * *